(12) United States Patent
Shimizu et al.

(10) Patent No.: US 7,842,510 B2
(45) Date of Patent: Nov. 30, 2010

(54) METHOD FOR MEASURING MATURITY DEGREE OF COMPOST AND MEASURING SOLUTION

(75) Inventors: Shinya Shimizu, Tsukuba (JP); Tokuo Matsushima, Sorachi-gun (JP)

(73) Assignee: Ryokusan Corporation Limited, Kanagawa (JP)

( * ) Notice: Subject to any disclaimer, the term of this patent is extended or adjusted under 35 U.S.C. 154(b) by 461 days.

(21) Appl. No.: 11/895,193

(22) Filed: Aug. 23, 2007

(65) Prior Publication Data
US 2009/0035871 A1    Feb. 5, 2009

(30) Foreign Application Priority Data
Aug. 24, 2006   (JP) .............................. 2006-227369

(51) Int. Cl.
G01N 21/00   (2006.01)
G01N 33/00   (2006.01)
G01N 33/24   (2006.01)

(52) U.S. Cl. .................... 436/164; 435/171; 435/41; 435/419; 435/410

(58) Field of Classification Search ................. 436/164; 435/171, 41, 419, 410
See application file for complete search history.

(56) References Cited

U.S. PATENT DOCUMENTS
4,131,428 A * 12/1978 Diggens ................... 205/778.5

FOREIGN PATENT DOCUMENTS
| JP | 09-127003 | 5/1997 |
| JP | 2000-109386 | 4/2000 |
| JP | 2002-162394 | 6/2002 |
| JP | 2003-207502 | 7/2003 |
| JP | 2004-201586 | 7/2004 |
| JP | 2004-226138 | 8/2004 |
| JP | 2005-274222 | 10/2005 |

OTHER PUBLICATIONS

Breslin, Vincent T., Degradation of Starch-Calcium Carbonate Disposable Packaging in a Solid Waste Compsoting Facility, 1998, Journal of Environmental Polymer Degradation, vol. 6, No. 1, 9-21.*

* cited by examiner

*Primary Examiner*—Vickie Kim
*Assistant Examiner*—Christine T Mui
(74) *Attorney, Agent, or Firm*—H. Henry Koda; William L. Androlia

(57) ABSTRACT

A method for measuring the maturity degree of a compost capable of determining the maturity degree of a compost purportedly of a product in a short period of time (10 to 30 minutes) by compost manufacturers, users and even those with insufficient expertise and experiences such as buyers in the distribution industry on site and also capable of determining it according to the maturity stage in an easy and cost-effective manner, and a measuring solution. A specific measuring solution is added to the compost to flocculate a compost extract containing humic-like substance and decomposed organic matter, and a liquid phase is acquired by precipitating the compost extract by the solid/liquid separation. Based on the correlation in which the absorbency of the liquid phase declines as the compost becomes more mature, the maturity degree of the compost is measured from the color contrasting density of the liquid phase.

9 Claims, 28 Drawing Sheets

Fig1A Correlation between the absorbance and biological, chemical, or physical properties of Compost sample

| Raw material | Age in week | Name of sample Region | (465nm) Absorbance | % Germination rate | % Root hair growth rate |
|---|---|---|---|---|---|
| Cow | 40w. | O town, Hokkaido | 0.06 | 100 | 104.2 |
| Cow | 20w. | H city, Kanagawa | 0.08 | 100 | 104.2 |
| Cow | Unknown | F city, Fukuoka | 0.17 | 100 | 93.3 |
| Cow | 8w. | C city, Chiba | 0.07 | 97.9 | 104.2 |
| Fatted | 18w. | N town, Tochigi | 0.45 | 57.5 | 0 |
| Fatted | 50w. | M city, Kagoshima | 0.19 | 83.83 | 0 |
| Fatted | 21w. | N town, Kagaoshima | 0.52 | 73.7 | 0 |
| Fatted | 14w. | S town, Hokkaido | 0.08 | 100 | 97.9 |
| Cow | | | | | |
| Cut grass, branch and leaf, food residue | 25w. | M city, Shimane | 0.06 | 100 | 104.1 |
| Cut grass, branch and leaf, food residue | 60w. | Y city, Shimane | 0.05 | 93.9 | 62.5 |
| Fish residue, hen excreta | Product | I city, Mie | 1.52 | 17.1 | 0 |
| Recommended standard items of compost and reference value (Zen-noh) | | | | 80% or more | 80% or more |

Fig1B

| % Moisture content | pH | mS/cm EC | dry% Organic matter content | dry% Organic carbon | dry% Phosphonic acid | dry% K(K2O) |
|---|---|---|---|---|---|---|
| 64.4 | 8.90 | 2.35 | 55.6 | 23.85 | 2.54 | 2.21 |
| 64.7 | 8.36 | 1.89 | 68.3 | 25.57 | 2.52 | 1.33 |
| 74.9 | 9.09 | 3.40 | 80.1 | 36.38 | 2.70 | 2.77 |
| 34.0 | 8.71 | 2.93 | 55.8 | 24.72 | 2.06 | 2.02 |
| 33.9 | 9.14 | 11.70 | 72.5 | 28.84 | 7.62 | 3.31 |
| 33.4 | 9.09 | 9.41 | 72.7 | 32.08 | 7.63 | 2.13 |
| 44.4 | 9.30 | 8.65 | 77.2 | 35.67 | 6.61 | 2.14 |
| 58.9 | 7.80 | 4.86 | 74.0 | 36.53 | 2.79 | 3.16 |
| 52.2 | 8.06 | 1.11 | 51.5 | 28.60 | 2.45 | 1.02 |
| 23.5 | 8.94 | 3.02 | 27.9 | 19.47 | 1.52 | 1.08 |
| 23.3 | 8.49 | 13.86 | 54.0 | 26.58 | 11.48 | 3.31 |
| 70% or less | 8.5 or less | 5ms or less | 60% or more | | 1% or more | 1% or more |

Fig1C

| Ca(CaO) dry% | Mg(MgO) dry% | Total nitrogen dry% | C/N ratio (—) | NH4-N mg/100g | NO3-N mg/100g | Maturity degree Number of items correlated |
|---|---|---|---|---|---|---|
| 1.36 | 0.86 | 1.32 | 18.1 | 12.8 | 2.0 | 8 |
| 3.72 | 1.32 | 1.33 | 19.2 | 5.2 | 26.6 | 10 |
| 1.89 | 0.78 | 2.31 | 15.7 | 45.1 | 24.9 | 8 |
| 1.68 | 0.79 | 1.65 | 15.0 | 27.4 | 1.1 | 8 |
| 2.95 | 2.00 | 2.53 | 11.4 | 198.5 | 0.7 | 6 |
| 2.55 | 1.75 | 2.13 | 15.1 | 151.2 | 78.9 | 7 |
| 1.30 | 1.69 | 2.55 | 14.0 | 199.4 | 0.0 | 6 |
| 1.37 | 0.46 | 1.59 | 23.0 | 78.6 | 31.99 | 10 |
| 3.25 | 0.62 | 2.41 | 11.9 | 6.3 | 20.0 | 9 |
| 15.79 | 0.48 | 1.71 | 11.4 | 151.7 | 2.38 | 7 |
| 15.94 | 1.41 | 3.29 | 8.1 | 570.1 | 5.4 | 6 |
| 1% or more | | | 30 or less | | | 10 |

Fig1D

| Correlation matrix | Absorbance | Germination rate | Root hair growth rate | Moisture content | pH | EC | Organic matter content | Organic carbon |
|---|---|---|---|---|---|---|---|---|
| Absorbance | 1.000 | | | | | | | |
| Germination rate | -0.963 | 1.000 | | | | | | |
| Root hair growth rate | -0.657 | 0.778 | 1.000 | | | | | |
| Moisture content | -0.468 | 0.604 | 0.642 | 1.000 | | | | |
| pH | 0.078 | -0.174 | -0.532 | -0.220 | 1.000 | | | |
| EC | 0.814 | -0.904 | -0.919 | -0.579 | 0.325 | 1.000 | | |
| Organic matter content | 0.024 | -0.003 | -0.193 | 0.489 | 0.145 | 0.272 | 1.000 | |
| Organic carbon | 0.040 | 0.026 | -0.181 | 0.418 | -0.007 | 0.229 | 0.855 | 1.000 |
| Phosphoric acid | 0.873 | -0.925 | -0.882 | -0.520 | 0.260 | 0.963 | 0.254 | 0.200 |
| K(K2O) | 0.547 | -0.564 | -0.407 | -0.032 | 0.080 | 0.683 | 0.529 | 0.478 |
| Ca(CaO) | 0.546 | -0.543 | -0.295 | -0.629 | -0.033 | 0.297 | -0.702 | -0.552 |
| Mg(MgO) | 0.461 | -0.589 | -0.804 | -0.308 | 0.537 | 0.750 | 0.477 | 0.187 |
| Total nitrogen | 0.813 | -0.813 | -0.701 | -0.424 | 0.195 | 0.747 | 0.137 | 0.290 |
| C/N ratio | -0.604 | 0.673 | 0.572 | 0.699 | -0.358 | -0.497 | 0.429 | 0.345 |
| NH4-N | 0.956 | -0.960 | -0.752 | -0.641 | 0.130 | 0.859 | -0.100 | -0.027 |
| NO3-N | -0.225 | 0.215 | -0.089 | 0.135 | -0.115 | 0.038 | 0.374 | 0.397 |
| Maturity degree | -0.607 | 0.712 | 0.848 | 0.667 | -0.745 | -0.750 | 0.071 | 0.070 |

Fig1E

| Phosphoric acid | K(K2O) | Ca(CaO) | Mg(MgO) | Total nitrogen | C/N ratio | NH4-N | NO3-N | Maturity degree |
|---|---|---|---|---|---|---|---|---|
| 1.000 | | | | | | | | |
| 0.585 | 1.000 | | | | | | | |
| 0.307 | -0.069 | 1.000 | | | | | | |
| 0.760 | 0.342 | -0.102 | 1.000 | | | | | |
| 0.797 | 0.429 | 0.354 | 0.462 | 1.000 | | | | |
| -0.540 | 0.017 | -0.628 | -0.319 | -0.756 | 1.000 | | | |
| 0.873 | 0.511 | 0.678 | 0.435 | 0.777 | -0.641 | 1.000 | | |
| 0.095 | -0.042 | -0.248 | 0.139 | -0.099 | 0.328 | -0.155 | 1.000 | |
| -0.700 | -0.322 | -0.375 | -0.604 | -0.669 | 0.757 | -0.684 | 0.274 | 1.000 |

[ Early composting ]　[ Middle mature compost ]　[ Late mature compost ]　[ Full mature compost ]

ABS:　　　　　　ABS:　　　　　　　ABS:　　　　　　ABS:
>0.35　　　　　　<0.35　　　　　　≒0.20　　　　　　≒0.10

Root hair growth rate :　Root hair growth rate :　Root hair growth rate :　Root hair growth rate :
≒50%　　　　　　≒50-70%　　　　　　≒60-80%　　　　　　>80%

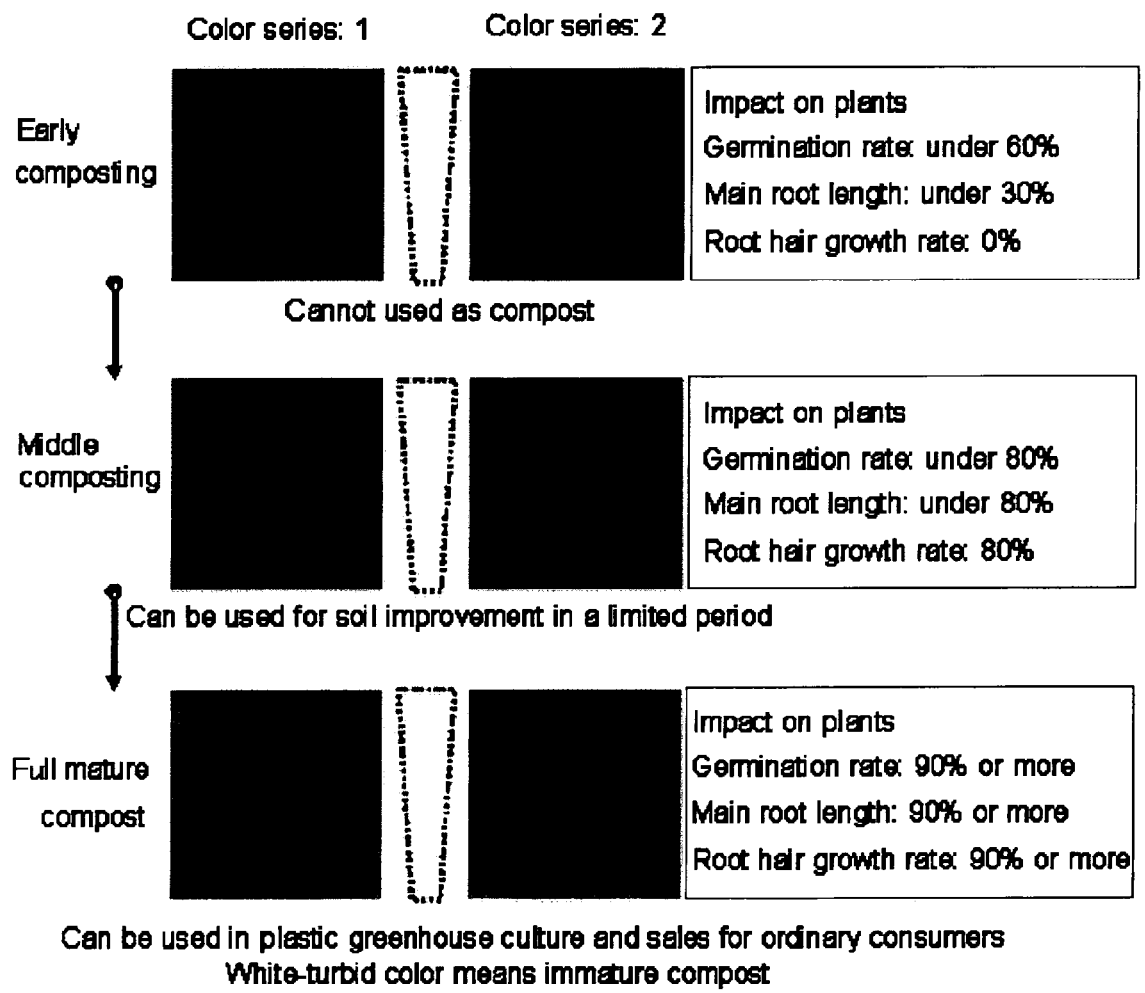
Fig3  Quick reference chart for measuring the maturity degree of compost
(The color becomes more transparent as compost becomes mature.)
Can be used in plastic greenhouse culture and sales for ordinary consumers
White-turbid color means immature compost

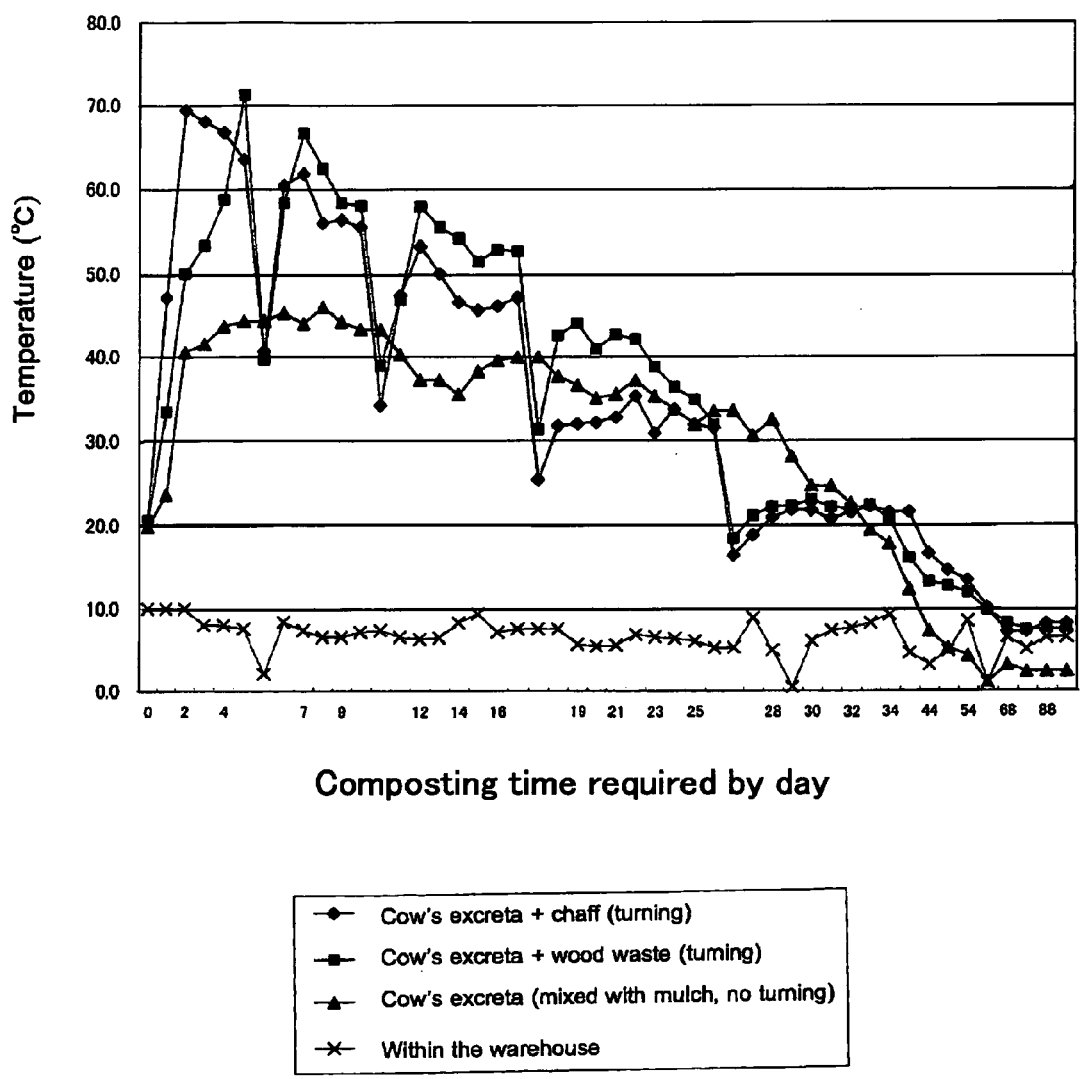

Fig5A Correlation between the absorbance and biological, chemical, or physical properties of Compost sample in a composting test

| Raw material | Composting time required by day | Absorbance | Germination rate | Root hair growth rate | Moisture content | pH | EC | Organic matter content | Organic carbon |
|---|---|---|---|---|---|---|---|---|---|
| A Cow's excreta + chaff Turning | 14 | 0.94 | 103.45 | 60.53 | 72.40 | 9.14 | 2.73 | 79.60 | 34.00 |
| | 21 | 0.30 | 103.45 | 73.68 | 71.90 | 9.04 | 2.89 | 79.30 | 33.90 |
| | 30 | 0.25 | 103.45 | 84.21 | 71.10 | 8.81 | 3.05 | 77.50 | 34.90 |
| | 61 | 0.21 | 100.00 | 77.00 | 70.50 | 9.00 | 3.15 | 77.80 | 34.00 |
| | 91 | 0.11 | 100.00 | 92.90 | 67.20 | 9.40 | 3.32 | 75.70 | 35.40 |
| B Cow's excreta + wood waste Turning | 14 | 0.59 | 100.34 | 73.68 | 73.40 | 9.10 | 2.73 | 85.00 | 36.40 |
| | 21 | 0.25 | 103.45 | 66.70 | 72.30 | 9.08 | 2.65 | 84.70 | 36.80 |
| | 30 | 0.21 | 103.45 | 78.95 | 72.30 | 8.72 | 2.77 | 84.30 | 37.70 |
| | 61 | 0.23 | 100.00 | 83.30 | 71.20 | 8.85 | 2.82 | 84.60 | 37.70 |
| | 91 | 0.08 | 100.00 | 85.70 | 67.60 | 9.41 | 3.04 | 84.00 | 39.90 |
| C Cow's excreta (mixed with mulch) No turning | 14 | 0.85 | 100.34 | 31.58 | 77.20 | 8.94 | 3.08 | 82.40 | 36.30 |
| | 21 | 0.51 | 103.45 | 52.63 | 76.30 | 8.94 | 3.40 | 80.50 | 35.60 |
| | 30 | 0.40 | 103.45 | 60.53 | 75.70 | 8.73 | 3.33 | 79.00 | 34.80 |
| | 61 | 0.35 | 100.00 | 58.00 | 73.70 | 8.87 | 3.43 | 80.20 | 35.30 |
| | 91 | 0.35 | 96.70 | 78.60 | 72.50 | 9.44 | 3.30 | 79.40 | 36.50 |
| Items for measuring maturity degree | | | 80% or more | 80% or more | 70% or more | 8.5 or less | 5ms or less | 60% or more | |

Fig5B

| Phosphoric acid | K(K2O) | Ca(CaO) | Mg(MgO) | C/N ratio | Total nitrogen | N-NH4 | N-NO3 | Maturity degree |
|---|---|---|---|---|---|---|---|---|
| 2.09 | 2.42 | 0.92 | 0.35 | 25.19 | 1.35 | 62.59 | 9.87 | 7 |
| 2.11 | 1.76 | 1.24 | 0.45 | 26.90 | 1.26 | 27.96 | 0 | 7 |
| 2.27 | 1.97 | 1.27 | 0.47 | 27.05 | 1.29 | 41.38 | 8.53 | 8 |
| 2.24 | 1.91 | 0.95 | 0.42 | 25.37 | 1.34 | 12.97 | 38.4 | 7 |
| 2.16 | 1.97 | 1.22 | 0.46 | 25.65 | 1.38 | 11.69 | 61.06 | 9 |
| 2.00 | 1.94 | 1.17 | 0.40 | 30.08 | 1.21 | 218.31 | 33.42 | 6 |
| 1.75 | 1.40 | 1.21 | 0.45 | 26.67 | 1.38 | 29.52 | 10.40 | 7 |
| 1.96 | 1.91 | 1.32 | 0.53 | 31.68 | 1.19 | 35.05 | 42.75 | 6 |
| 1.84 | 1.95 | 0.95 | 0.41 | 29.45 | 1.28 | 14.02 | 50.22 | 8 |
| 1.54 | 2.02 | 1.16 | 0.38 | 30.00 | 1.33 | 19.60 | 77.37 | 9 |
| 2.03 | 2.30 | 1.34 | 0.50 | 21.35 | 1.70 | 267.16 | 67.46 | 7 |
| 2.19 | 1.79 | 1.39 | 0.53 | 21.98 | 1.62 | 319.51 | 69.71 | 7 |
| 2.13 | 2.42 | toltu | 0.69 | 21.75 | 1.60 | 43.78 | 164.51 | 7 |
| 2.33 | 2.16 | 1.31 | 0.51 | 20.76 | 1.70 | 18.66 | 178.33 | 7 |
| 2.42 | 2.01 | 1.49 | 0.57 | 23.10 | 1.58 | 23.50 | 195.32 | 7 |
| 1% or more | 1% or more | | | 30% or less | 1% or more | | | 10 |

Fig5C

| Correlation matrix | Composting time required by day | Absorbance | Germination rate | Root hair growth rate | Moisture content | pH | EC | Organic matter content | Organic carbon |
|---|---|---|---|---|---|---|---|---|---|
| Composting time required by day | 1.0000 | | | | | | | | |
| Absorbance | -0.6289 | 1.0000 | | | | | | | |
| Germination rate | -0.7323 | 0.1498 | 1.0000 | | | | | | |
| Root hair growth rate | 0.5923 | -0.7615 | -0.2033 | 1.0000 | | | | | |
| Moisture content | -0.6660 | 0.6718 | 0.2475 | -0.8741 | 1.0000 | | | | |
| pH | 0.5897 | -0.1194 | -0.5653 | 0.3516 | -0.5470 | 1.0000 | | | |
| EC | 0.4585 | -0.1486 | -0.3323 | -0.1433 | 0.1435 | 0.0740 | 1.0000 | | |
| Organic matter content | -0.2506 | 0.0718 | 0.0145 | -0.1340 | 0.1745 | -0.1346 | -0.6141 | 1.0000 | |
| Organic carbon | 0.3605 | -0.3405 | -0.3066 | 0.2348 | -0.2511 | 0.2281 | -0.2173 | 0.7248 | 1.0000 |
| Phosphoric acid | 0.0361 | 0.1827 | -0.1707 | -0.1326 | 0.2859 | -0.1096 | 0.5904 | -0.7270 | -0.7152 |
| K(K2O) | 0.0041 | 0.5242 | -0.1271 | -0.3407 | 0.2621 | -0.1197 | 0.3038 | -0.2693 | -0.2005 |
| Ca(CaO) | -0.0370 | -0.0283 | 0.0539 | -0.2857 | 0.4888 | -0.1612 | 0.5406 | -0.1489 | 0.0043 |
| Mg(MgO) | -0.0205 | -0.0809 | 0.0694 | -0.2817 | 0.5265 | -0.3655 | 0.5787 | -0.2335 | -0.1318 |
| C/N ratio | 0.0382 | -0.4020 | 0.1052 | 0.6650 | -0.5707 | 0.0643 | -0.7209 | 0.5033 | 0.5031 |
| Total nitrogen | 0.0667 | 0.3400 | -0.2351 | -0.6949 | 0.5979 | -0.0408 | 0.7294 | -0.2392 | -0.1534 |
| N-NH4 | -0.5359 | 0.6200 | 0.1230 | -0.6603 | 0.6777 | -0.1425 | 0.0903 | 0.2262 | -0.0136 |
| N-NO3 | 0.4817 | -0.0605 | -0.5322 | -0.1656 | 0.2565 | 0.0918 | 0.7203 | -0.1583 | 0.1100 |
| Maturity degree | 0.6457 | -0.4645 | -0.2307 | 0.4606 | -0.6727 | 0.4575 | 0.2722 | -0.3091 | 0.2601 |

Fig5D

| | Phosphoric acid | K(K2O) | Ca(CaO) | Mg(MgO) | C/N ratio | Total nitrogen | N-NH4 | N-NO3 | Maturity degree |
|---|---|---|---|---|---|---|---|---|---|
| | 1.0000 | | | | | | | | |
| | 0.2554 | 1.0000 | | | | | | | |
| | 0.3211 | 0.1467 | 1.0000 | | | | | | |
| | 0.4291 | 0.2169 | 0.9150 | 1.0000 | | | | | |
| | -0.8092 | -0.3899 | -0.4703 | -0.5285 | 1.0000 | | | | |
| | 0.4117 | 0.3835 | 0.5653 | 0.5772 | -0.9268 | 1.0000 | | | |
| | 0.0435 | 0.0604 | 0.2032 | 0.0767 | -0.2814 | 0.3486 | 1.0000 | | |
| | 0.3964 | 0.4138 | 0.6323 | 0.6719 | -0.5716 | 0.7129 | -0.0890 | 1.0000 | |
| | -0.2573 | 0.0213 | -0.1888 | -0.2542 | 0.0658 | -0.0302 | -0.3492 | -0.0118 | 1.0000 |

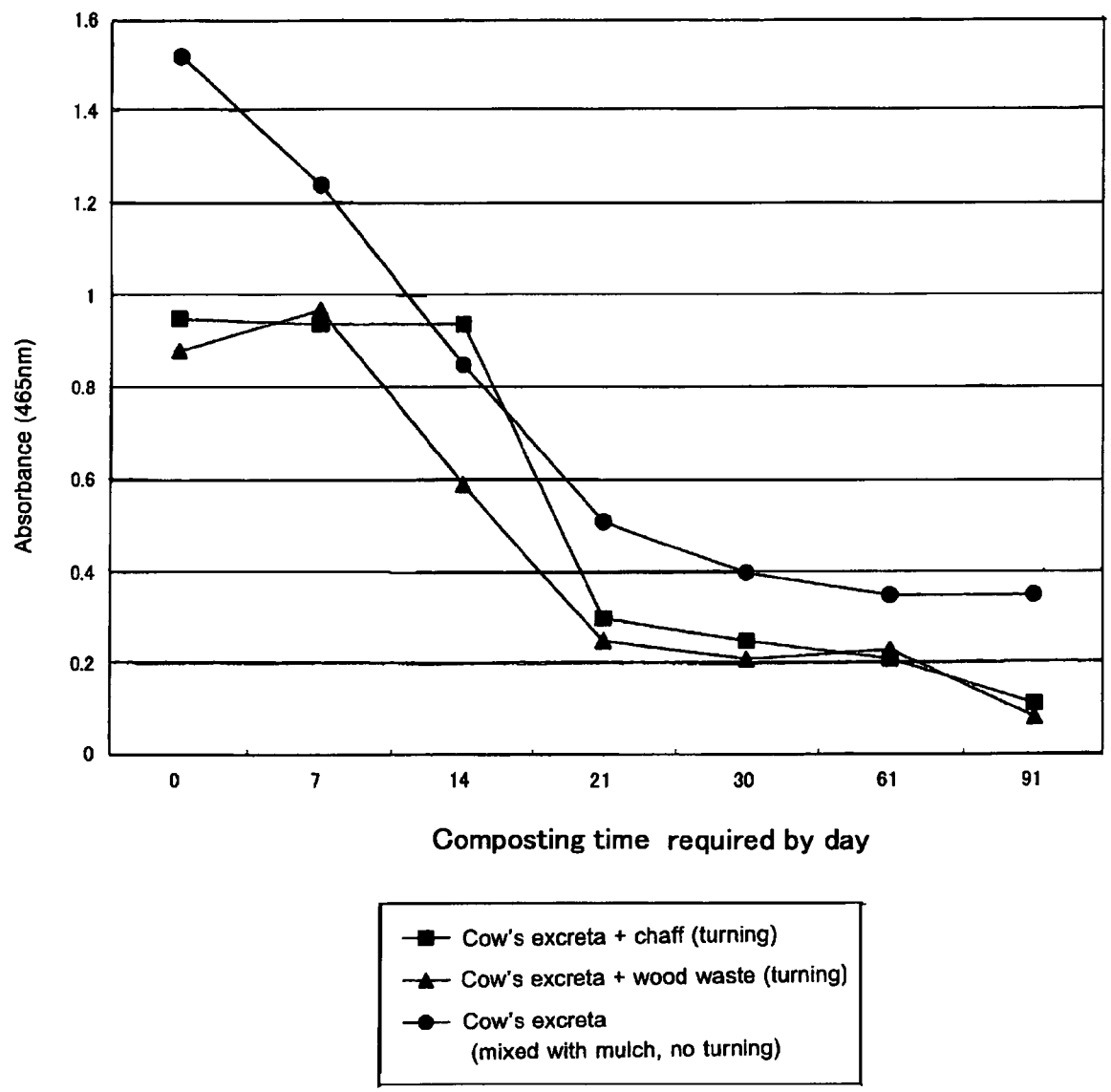

Fig7
(a) Product compost A
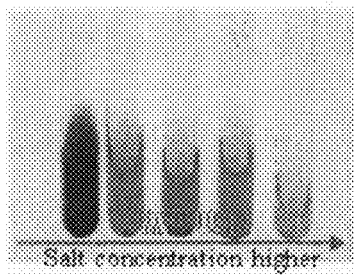
(b) Product compost B
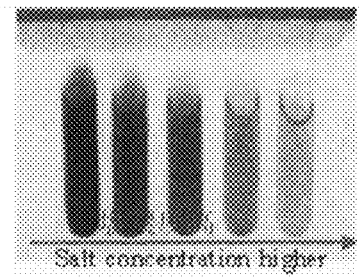
(c) Product compost C
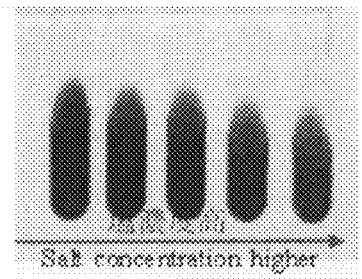
The salt concentrations are 0.000 (D.W.), 0.767M, 1.535M, 3.070M and 6.100M from left.

Acetic acid-sodium acetate buffer solution and salt concentration

Acetic acid-sodium acetate buffer solution and pH

Fig14

| Name of sample | Composting time required by day | Raw material | Absorbance | Germination rate | Root hair growth rate |
|---|---|---|---|---|---|
| Compost E | 150d. | Cow's excreta and subsidiary material | 0.069 | 100.0 | 85.7 |
| Compost F | 120d. | Cow's excreta and subsidiary material | 0.026 | 100.0 | 100.0 |
| Compost G | 300d. | Cow's excreta and subsidiary material | 0.033 | 100.0 | 100.0 |
| Compost H | 150d. | Fatted cow's excreta and wood waste | 0.328 | 75.9 | 0.0 |

Fig15
(a) Relationship between absorbance and germination rate pH4
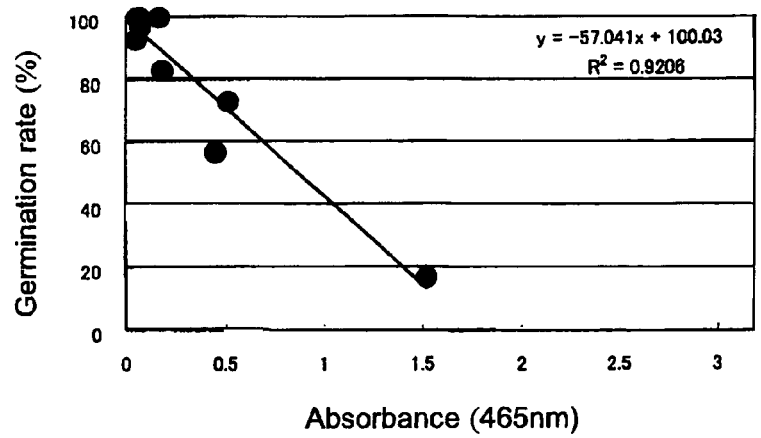
(b) Relationship between absorbance and germination rate pH5
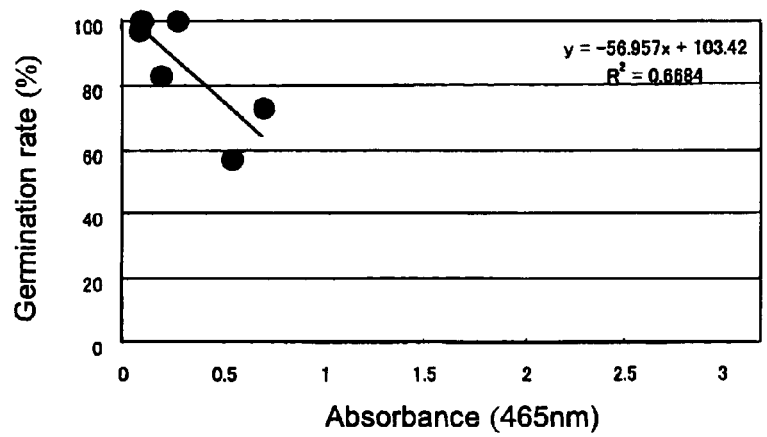
(c) Relationship between absorbance and germination rate pH8
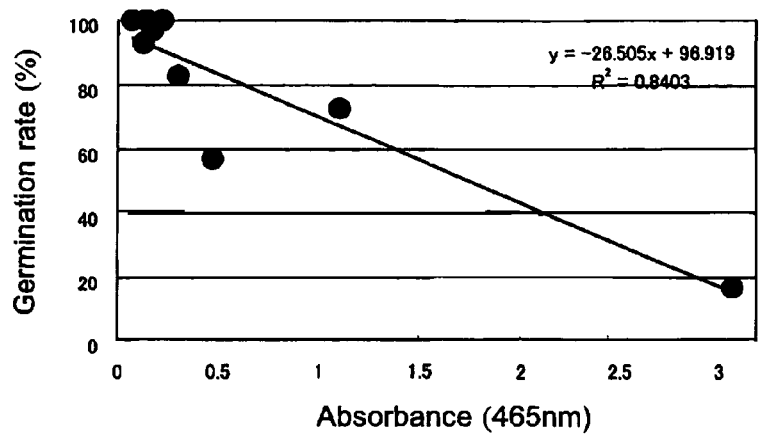

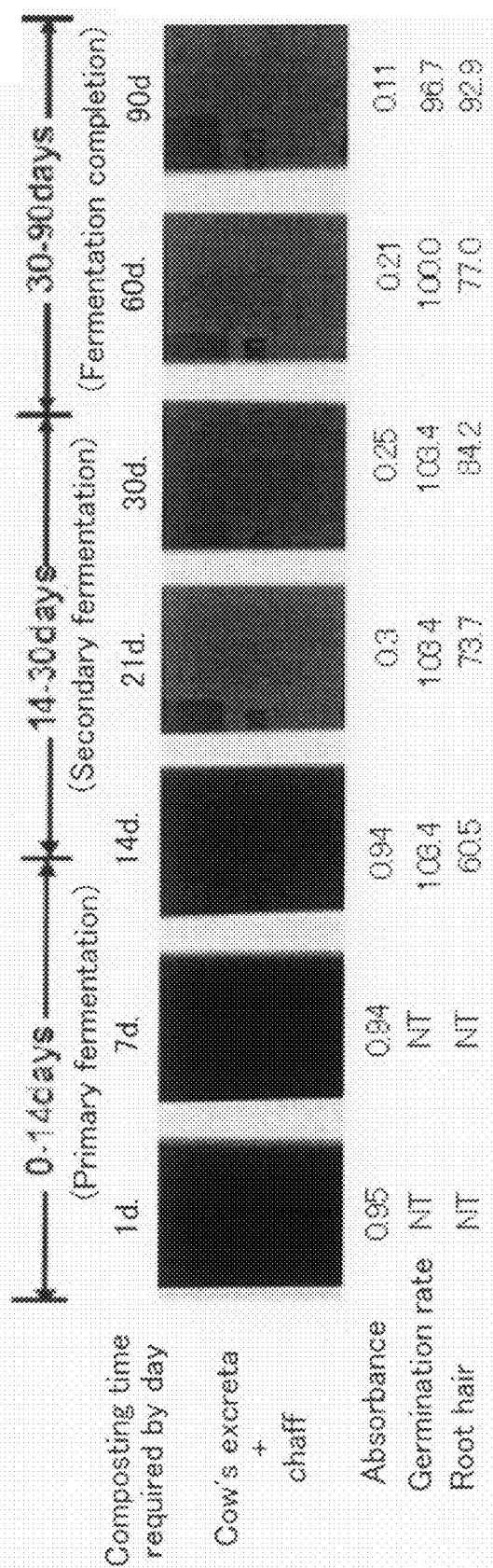
Fig 16A Change in color and absorbance (465nm) of extract by the composting of cow's excreta

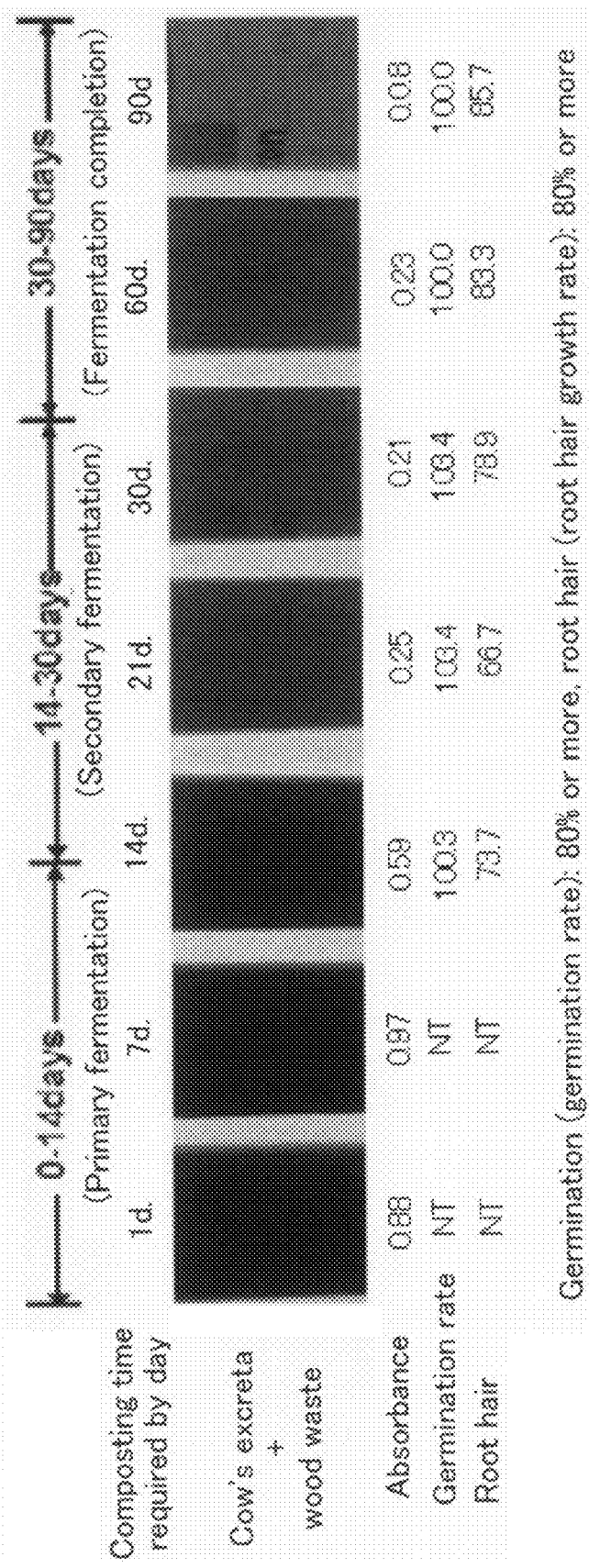

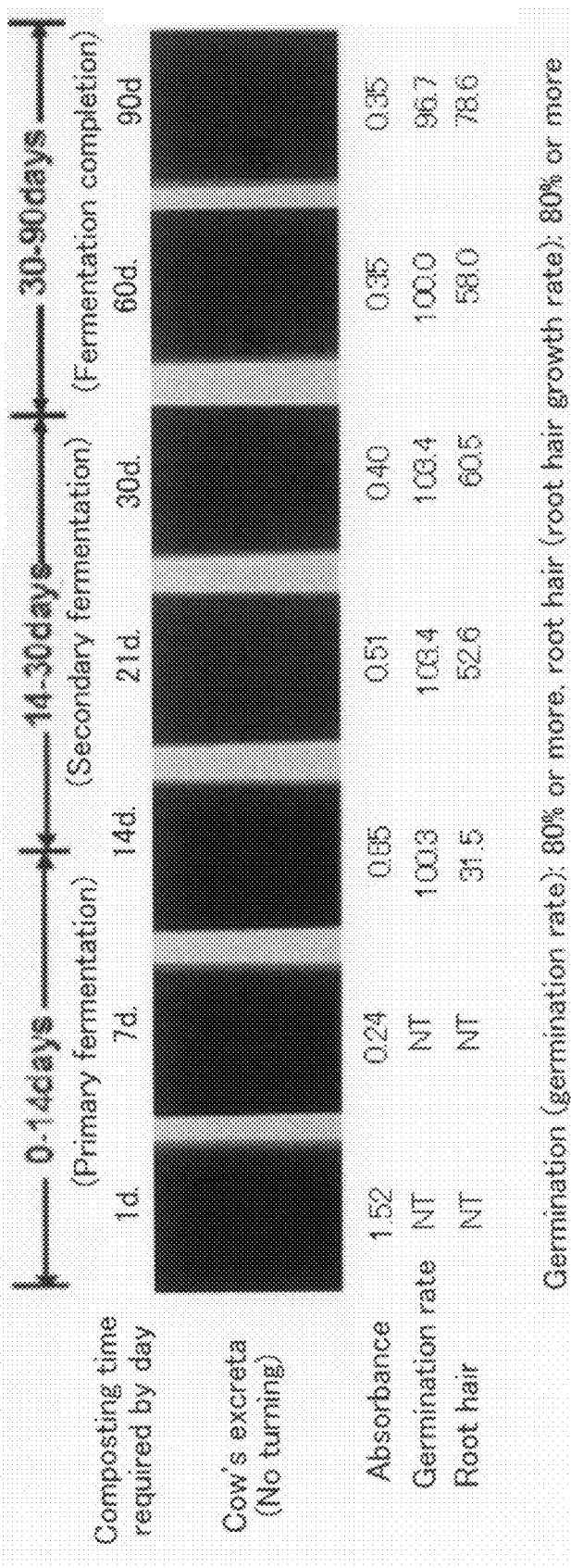

Fig17

| No. | Material | Composting time required by day | Absorbance | Germination rate |
|---|---|---|---|---|
| MTR A | Food residue, wood waste | 365 d. | 0.094 | 96.7 |
| MTR B | Food residue, wood waste | 180 d. | 0.095 | 93.3 |
| MTR C | Food residue, wood waste | 30 d. | 0.293 | 40.0 |
| MTR D | Food residue, wood waste | 30 d. | 0.497 | 13.3 |

| No. | Main root length rate | Root hair growth rate | pH | EC |
|---|---|---|---|---|
| MTR A | 125.4 | 90.0 | 7.91 | 0.90 |
| MTR B | 114.7 | 90.0 | 8.00 | 1.01 |
| MTR C | 0.0 | 0.0 | 8.87 | 2.11 |
| MTR D | 0.0 | 0.0 | 8.63 | 2.82 |

| No. | Moisture content | T-N | $NH_4$-N | $NO_3$-N |
|---|---|---|---|---|
| MTR A | 54.5 | 2.200 | 18.640 | nd |
| MTR B | 51.9 | 2.050 | 1.170 | nd |
| MTR C | 25.5 | 2.390 | 332.640 | nd |
| MTR D | 52.4 | 2.320 | 427.550 | nd |

| No. | $P_2O_5$ | $K_2O$ | C/N | Organic matter content |
|---|---|---|---|---|
| MTR A | 3.390 | 0.635 | 11.300 | 48.900 |
| MTR B | 3.810 | 0.888 | 11.800 | 49.000 |
| MTR C | 3.860 | 1.300 | 10.300 | 52.800 |
| MTR D | 4.110 | 0.335 | 13.000 | 65.100 |

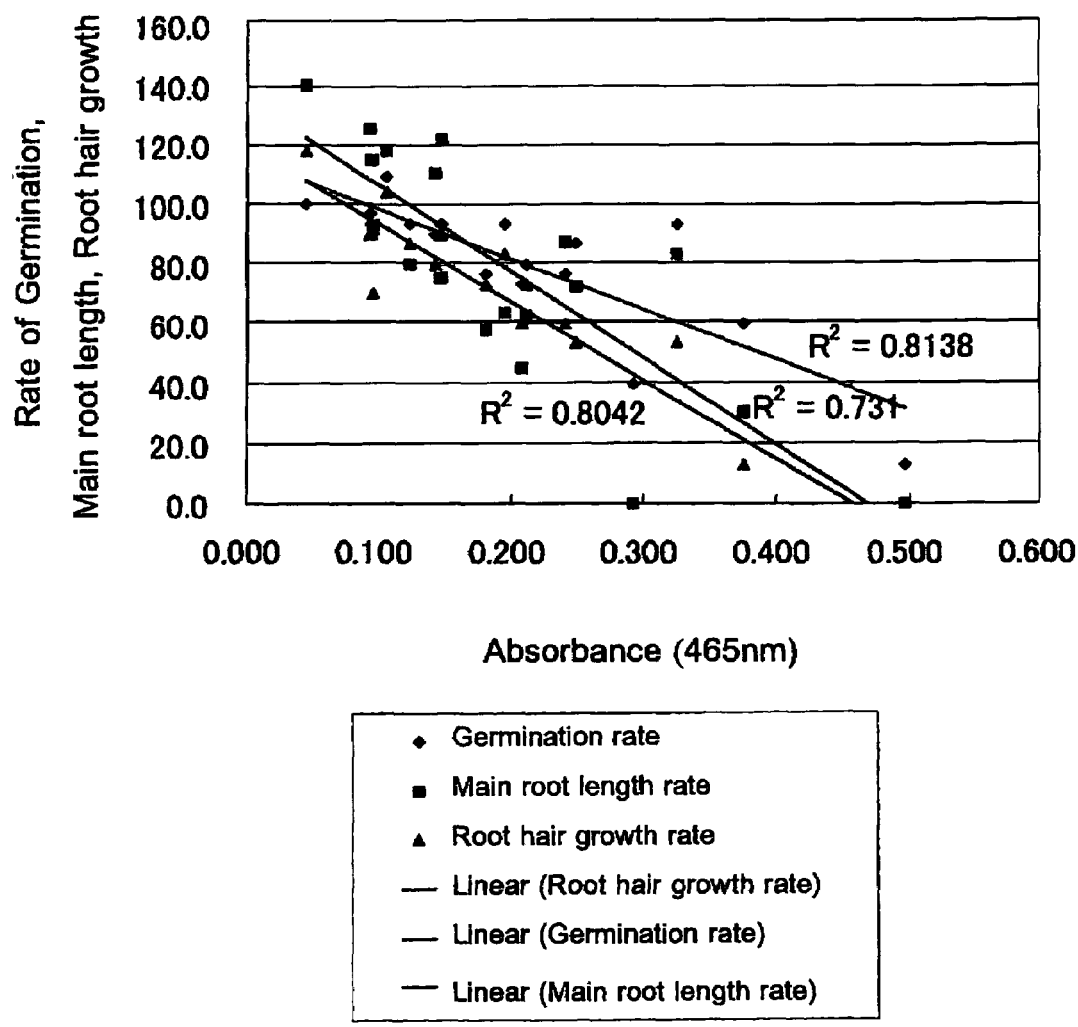
Fig18 Absorbance and phytotoxicity test

Fig19

| Classification of maturity degree | Absorbance ABS:465nm | Germination rate % | Main root length rate % |
|---|---|---|---|
| Average full maturity (absorbance<0.11) | 0.079 | 97.57 | 88.87 |
| Average middle maturity (0.11<0.35) | 0.198 | 83.86 | 62.43 |
| Average immaturityt (>0.35) | 0.675 | 66.43 | 22.90 |
| Proper value | — | 80% or more | 80% or more |

| Classification of maturity degree | Root hair growth rate % | pH | EC mS/cm | Moisture content % |
|---|---|---|---|---|
| Average full maturity (absorbance<0.11) | 95.78 | 8.21 | 2.63 | 53.16 |
| Average middle maturity (0.11<0.35) | 61.83 | 8.79 | 2.98 | 61.05 |
| Average immaturityt (>0.35) | 17.86 | 8.51 | 5.82 | 58.47 |
| Proper value | 80% or more | 8.5 or less | 5.0 or less | 70% or less |

| Classification of maturity degree | T-N % | P2O5 % | K2O % | C/N |
|---|---|---|---|---|
| Average full maturity (absorbance<0.11) | 1.54 | 2.39 | 1.91 | 16.91 |
| Average middle maturity (0.11<0.35) | 1.95 | 3.02 | 2.16 | 16.92 |
| Average immaturityt (>0.35) | 2.19 | 4.13 | 2.17 | 16.79 |
| Proper value | 1.0% or more | 1.0% or more | 1.0% or more | 30 or less |

| Classification of maturity degree | Organic matter content % | NH4 mg/100g | NO3 mg/100g |
|---|---|---|---|
| Average full maturity (absorbance<0.11) | 52.06 | 19.48 | 9.50 |
| Average middle maturity (0.11<0.35) | 70.93 | 149.90 | 16.97 |
| Average immaturityt (>0.35) | 76.07 | 500.17 | 3.87 |
| Proper value | 60% or more | — | — |

METHOD FOR MEASURING MATURITY DEGREE OF COMPOST AND MEASURING SOLUTION

BACKGROUND OF THE INVENTION

1. Field of the Invention

The present invention generally relates to a method for measuring the maturity degree of a compost and a measuring solution, and deals more particularly with a method for measuring the maturity degree of a produced compost by compost manufacturers, distributors and users on site in a swift, easy and cost-effective manner, and a measuring solution.

2. Description of the Related Art

With recent growing environmental concerns in recycle-based society for efficient use of limited resources, the biomass (renewable organic resource) from animals and plants is focused and its use is demanded. In particular, by composting unused resources like livestock excreta and food waste, such processed materials will be reused as biomass resources in the recycle-based society.

Currently, Japan produces a large amount of livestock excreta exceeding 90 million ton a year. Under the circumstances, facilities for composting and recycling the livestock excreta are proactively established and introduced, as well as composting centers by individual agricultural areas to compost and recycle most of such livestock excreta.

Composting livestock excreta to produce mature materials is aimed at improving physical properties of the excreta by changing its ill-favored appearance, reducing odor and the degree of moisture content so that users can easily handle, as well as recycling it into biomass. Meanwhile, the biodegradation of easily decomposable organic matter such as proteins and sugars in a smaller volume, with no harm to crops if applied thereto, however, is strongly demanded to produce composts with no obstruction to germination or growth inhibition on crops.

Currently, environmentally friendly type of agriculture is proactively performed by a technology for treating and utilizing livestock excreta. Since composts from the livestock excreta are normally provided in an insufficiently, mature stage compost users cannot find reliability in such livestock excreta-derived composts, resulting in a limited use and shipment of product composts.

The immaturity in shipped product composts is caused by incomplete methods for measuring the maturity degree of a compost. Conventionally, the quality of product composts is empirically managed and assessed, mainly based on composting time required (period of time), compost's condition of color tone, odor, shape and texture, that allows for no specific, unified and precision-reliable approaches. It is particularly difficult to find the difference between a dried immature compost and mature compost from appearance.

As shown in the above descriptions, there are various types of techniques for assessing compost quality, thereby generating significantly different compost qualities among many composting centers and individual livestock farmers as compost manufacturers and providers. Thus, commercially available composts include immature composts.

Meanwhile, a use of immature composts and inappropriate treatment of livestock excreta can cause gas damage and nitrogen starvation by rapid decomposition in the soil and poor plant growth by a growth-inhibiting substance, resulting in significant adverse impacts on farm administration. Also, handling these materials can provide a source of zoonoses such as cryptosporidium (protozoan), pathogenic *E. coli* bacillus and *salmonella*. In addition to malodors, water pollution, due to eutrophication in closed water areas by the discharge of the zoonoses into rivers or nitrate nitrogen by their penetration into underground water, is a serious drawback in environmental conservation.

According to surveys by the Ministry of the Environment, many well water facilities that don't fulfill environmental water quality standards in nitrate nitrogen-containing underground water are found in agricultural and livestock areas. It is, therefore, suggested that excessive fertilizer application in agricultural land and inappropriate treatment of livestock excreta and domestic wastewater have significantly adverse impacts on the water quality of surrounding water areas.

The nitrate nitrogen in underground water or fresh vegetables can cause humans excessive consumption of nitrate, and particularly human infants and ruminants (like cows and bulls) methemoglobinemia (cyanosis), called as blue baby syndrome that impairs the ability to supply oxygen throughout the body with fatal impacts. Recently, the blue baby syndrome has become a big social issue, and its cases total more than 3,000 throughout the world.

The definition of full maturity is described as follows. Nutrients (easily decomposable organic matter) in raw materials are decomposed by aerobic microorganisms, and composted materials should be heated by heat of decomposition in windrow turning system at 55° C. for 2 weeks or more and in passive system at 55° C. for 3 days or more. The resulting mature composts will show no reheating, phytotoxicity, mixture of weed seed, or animal-and-plant pathogenic bacteria therein, ensuring product safety. Additionally, the process of full maturity is characterized by a rapid decline in ammonium nitrogen, slow increase in nitrate nitrogen and decline in total nitrogen. Nowadays, more and more consumers are concerned with food reliability and safety, and particularly with organic farming. In order to produce reliable agricultural crops for consumers, the importance of composting is currently realized in view of maintenance of soil fertility. There is a growing concern about resource-recycling agriculture to achieve recycle-based society, by using mature composts from livestock excreta, etc. In addition, farm households with advanced agricultural techniques are more interested in the use of full composts in farm production.

To establish resource-recycling agriculture in farming, particularly livestock and ackerland farming, the establishment of a system for supplying full mature composts is required. Though the maintenance of such a system needs a technique for measuring the maturity degree of a compost, such a technique (a.k.a. quality management method) has not been established. Currently, public research organizations study and develop methods for measuring the maturity degree of a compost in a more objective manner.

Specifically, such methods include chemical property analysis, seedling test, easier and quicker germination test, seed-pack root elongation test, use of seedling culture apparatus, methylene blue colorimetric method, Analysis of amino acid by paper chromatography, *E. coli* culture test, a method for chemically measuring nitrogen, phosphorus, potassium, pH and EC in the compost, a method for BOD (Biochemical Oxygen Demand) in the compost (compotester), liquid chromatography method and far-infrared ray method.

Among other things, the method for measuring the maturity degree of a product compost according to its temperature is disclosed in a research result, "Simple Evaluation and Use of the Quality and Components in Compost from Livestock Excreta (Garbage-derived Compost)" conducted by National Agriculture and Food Research Organization and National Agricultural Research Center.

This study focused on fluctuations of temperature in the composting process. More specifically, after a product compost is heated up to 60° C. or more, and as the compost is repeatedly turned, the temperature gradually declines, approaches and corresponds closely to outside air temperature. Then, the compost can be determined to be full mature. Thus, using the fluctuations of temperature data in a product compost, its maturity completion can be determined, and this decision can be made only by measuring the temperature.

Also, methylene blue calorimetric method is disclosed as a relatively easy method for measuring the maturity degree of a compost. In this method, after a solvent is added to a weighed compost sample and stirred, it is filtered and a reaction reagent containing a methylene blue pigment is added thereto. By incubating it in a thermostatic chamber at 35° C. for 24 hours and estimating dissolved oxygen (DO) amount consumed due to the biodegradation of organic matter, the maturity degree of a compost can be determined.

SUMMARY OF THE INVENTION

Despite the above-mentioned technological advantages, conventional methods for measuring the maturity degree of a compost require an analyzer for this purpose. In fact, the maturity of a sampled compost cannot be measured on site and instead the compost must be taken to an analysis facility for measurement. In addition, the measurement of the maturity degree requires long hours of complicated compost extraction and pretreatment processes. Advanced specialized technique and expensive special analyzers required in the analysis can be applied only to particular raw materials in some properties to be analyzed. The analysis results are significantly affected by types of raw materials used. Also, repeatability depends on a type of raw material and it can be unstable and unfavorable. Also, repeatability depends on a type of raw material and it can be unstable and unfavorable. Meanwhile, there is a plurality of drawbacks with existing development technologies, such as low reliability in measured values, in raw materials containing substances that inhibit the measurement.

In consideration of compost's applicability, reliability, simplicity and handleability, there are a limited number of reliable methods for measuring the maturity degree of a compost, thereby providing no established and unified measurement of the maturity degree and quality management in compost production, transportation and use.

Additionally, conventional compost quality assessment methods don't necessarily focus on the entire compost maturity, but on limited biological or chemical properties such as germination rate and EC value, demonstrating a disparity between biological and chemical properties in full mature composts. In order to accurately determine the maturity degree of a compost, it is necessary to comprehensively measure the maturity degree, not only with limited properties to be analyzed, but also with a plurality of methods combined for plurality of methods for measuring the maturity degree.

On the other hand, according to the method for determining maturity completion using the compost's temperature fluctuation data by National Agricultural Research Center, the maturity completion can be determined only by continually collecting the temperature data and achieving data construction. Despite this advantage, a compost purchaser cannot immediately find the maturity degree (quality) of a compost even after measuring its temperature. This is attributed to no continuously obtained temperature fluctuation data even in a product compost, thereby achieving no determination of maturity completion based on temperature data. In this method that will be effective only when raw materials are treated properly to achieve composting, it is extremely difficult to distinguish between an immature compost and full mature product compost in production and distribution sectors by measuring only compost temperature.

In addition, it is impossible to find out the maturity stage of a compost in the composting process, as well as the phase in full maturity.

The invention disclosed in the Japanese Unexamined Patent Publication No. 2002-162394 must have many working processes, as mentioned above, such as weighing of a compost sample, addition of a sample preparation, filtration, addition of a reaction reagent to an extract, extraction of the extract, incubation of the extract in a thermostatic chamber at 35° C. for 24 hours and measurement of the maturity degree with a color sample or colorimeter. Since expertise and specialized experience are required in these processes, compost manufacturers or users are unable to measure the maturity degree of a compost in its manufacturing process.

Due to required weighing of a composted material and its incubation in the thermostatic chamber for 24 hours, a compost must be collected and transported to an analysis chamber, thereby taking a longer time for the measurement. Thus, this method cannot be a simple and swift method.

To solve the aforementioned problems, it is, therefore, one object of the present invention to provide a method for measuring the maturity degree of a compost capable of determining the maturity degree in a short period of time (10 to 30 minutes) by compost manufacturers, users and even those with insufficient expertise and experiences such as buyers in the distribution industry and also capable of determining it according to the maturity stage in an easy and cost-effective manner, and a measuring solution.

The method for measuring the maturity degree of a compost according to the present invention is characterized by adding a predetermined measuring solution to said compost to flocculate a compost extract containing humic-like substance and decomposed organic matter and obtaining a liquid phase by precipitating said compost extract by the solid/liquid separation and measuring the maturity degree of said compost from the color contrasting density of said liquid phase, based on the correlation in which the absorbancy of said liquid phase declines as said compost becomes more mature.

In this invention, it is also possible to measure the maturity degree of said compost from the color contrasting density of said liquid phase, based on the correlation in which the absorbancy of said liquid phase declines according to nitrogen transformation that causes nitrate nitrogen as ammonium nitrogen decreases, in addition to conventional methods for measuring the maturity degree of a compost with reference to biological properties such as germination rate in said compost, chemical properties such as pH, EC and fertilizer components and physical properties such as moisture content.

Moreover, this invention can measure the maturity degree of said compost from the color contrasting density of said liquid phase, based on the correlation in which the absorbancy of said liquid phase declines as the growth rate of a plant root (main root and root hair) grown using said compost.

Said measuring solution in this invention is preferably a solution whose concentration of salt like sodium chloride ranges from 0.2M to 2.0M.

Furthermore in this invention, said measuring solution preferably has a pH value of 7.0 or less according to salt concentration.

The method for measuring the maturity degree of a compost according to the present invention can use a colorimetric sheet (sample) by which the color contrasting density of said liquid phase and the maturity degree of said compost are associated with each other.

The measuring solution according to the present invention is characterized by being added to a compost to flocculate a compost extract containing humic-like substance and decomposed organic matter and obtaining a liquid phase and is a solution with a sodium chloride concentration ranging from 0.2M to 2.0M and a pH value of 7.0 or less.

Also, the measuring solution in this invention is characterized by being added to a compost to flocculate a compost extract containing humic-like substance and decomposed organic matter and obtaining a liquid phase to visually measure the maturity degree and preferably is a 0.2M acetic acid-sodium acetate buffer solution with a sodium chloride concentration of 1.0M and with a pH value of 4.0.

According to the present invention, this method can measure the maturity degree of a compost purportedly of a product capable of determining the maturity degree in a short period of time (10 to 30 minutes) by compost manufacturers, users and even those with insufficient expertise and experiences such as buyers in the distribution industry on site and also capable of determining the maturity degree according to the maturity stage in an easy and cost-effective manner. Accordingly, this method can properly treat livestock excreta and provide an appropriate indicator in the use of compost, thereby preventing environmental pollution from excessive nitrate nitrogen due to the application of immature composts. In addition, the use of higher-quality composts can produce reliable foods and also win trust of consumers in food safety.

BRIEF DESCRIPTION OF THE DRAWINGS

The above and other objects of the invention will be seen by reference to the description taken in connection with the accompanying drawings, in which:

FIGS. 1A through 1E illustrating the correlation among biological, chemical and physical properties and the absorbency in composted materials having different raw materials and regional characteristics;

FIG. 3 is a diagram illustrating a sample quick reference chart for measuring the maturity degree of a compost using a measuring solution;

FIG. 4 is a graph showing the temperature fluctuation in a composting test in Example 1;

FIGS. 5A through 5D are tables showing the correlation among composting time required by day, biological, chemical and physical properties and the light absorbency in Example 1;

FIG. 6 is a graph showing the change in absorbancy in the composting test in Example 1;

FIG. 7 is a digital photographic image showing the color contrasting density when concentration of salt is changed in experiment 1 for obtaining the optimum salt concentration for a measuring solution in Example 2, and (a) is a digital photographic image for product compost A, (b) is a digital photographic image for product compost B and (c) is a digital photographic image for product compost C;

FIG. 14 is a table showing the results of the absorbancy, germination rate and root hair growth rate for each compost in Example 2;

FIG. 15 is a graph showing the relationship between pH and phytotoxicity for a measuring solution in Example 2, and (a) is a graph for pH4.0, (b) is a graph for pH5.0 and (c) is a graph for pH8.0;

FIGS. 16A through 16C are graphs showing the absorbancy and phytotoxicity for composts having different raw materials in Example 3;

FIG. 17 is a table showing the relationship among biological, chemical and physical properties and the absorbancy in a food residue-derived compost in Example 3;

FIG. 18 is a graph showing the relationship between the absorbancy in a compost liquid phase acquired using a measuring solution in Example 4 and phytotoxicity; and FIG. 19 is a table showing the maturity degree according to compost properties and absorbancy in Example 6.

DETAILED DESCRIPTION OF THE PREFERRED EMBODIMENT

Figure 2:
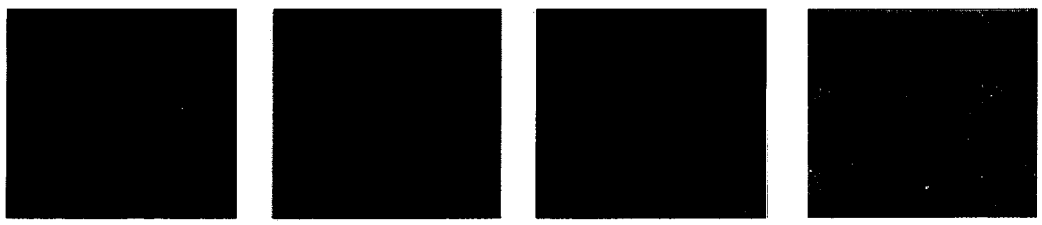
FIG. 2 is a diagram illustrating the relationship among the maturity degree of a compost, the color of a compost liquid phase and the absorbancy.

The method for measuring the maturity degree of a compost and measuring solution according to the present invention will be described.

The method for measuring the maturity degree of a compost according to the present invention is a method, in which a predetermined measuring solution is added to a compost to flocculate a compost extract containing humic-like substance and decomposed organic matter and a liquid phase is acquired by precipitating the compost extract by the solid/liquid separation to visually measure the maturity degree of the compost from the color contrasting density of the liquid phase (color contrasting density).

In a conventional method for extracting humic-like substance, alkali is extracted from soil, compost, etc. and acid-precipitated at a pH value of about 1.0. The method in this invention is significantly different from the conventional one, in that a predetermined measuring solution is added to an extract of humic-like substance in a compost or a liquid containing a standard humic-like substance to extract and flocculate the humic-like substance.

The absorbancy of the compost liquid phase obtained can be measured by a spectrophotometer. The maturity degree of the compost can be visually measured by the maturity stage from the color contrasting density of a supernatant after a compost extract is solid-liquid separated according to certain extraction conditions.

The relationship between the maturity degree of a compost and the absorbancy or color contrasting density is described. Specifically, the absorbancy of the compost liquid phase declines as the maturity degree becomes higher and the hue becomes dark brown and then transparent amber color.

Also, nitrogen transformation was confirmed with a considerable reduction in ammonium nitrogen in the compost and the appearance of nitrate nitrogen according to composting. This nitrogen transformation indicates full maturity in the compost. The nitrate nitrogen increases as a material is composted, but then decreases. The change (decline) in absorbancy of the compost liquid phase was observed in nitrogen transformation. More specifically, based on the correlation with the change in nitrogen form used in conventional measuring methods, the absorbancy or color contrasting density of the compost liquid phase is observed to measure the maturity degree of a compost therefrom.

Moreover, growth inhibition on plants is conventionally used in measuring the maturity degree of a compost in a phytotoxicity test. In this embodiment, the growth rate of a main root or root hair in a plant grown using said compost increases as the absorbancy of the compost liquid phase declines.

As shown in FIG. 1, a multivariate analysis of maturity degrees such as absorbancy, germination rate, growth rate of root hair, moisture content, pH, EC, organic substance content, organic carbon, K (K2O), CA (CaO), phosphoric acid, MG (MgO), C/N ratio, total nitrogen, N—NH4, N—NO3 suggests a positive or negative correlation between the absorbancy and germination rate, EC value, phosphoric acid, nitrogen or ammonium nitrogen.

The existing methods for measuring the maturity degree of a compost consider compost's biological, chemical and physical properties individually, therefore they are unable to comprehensively measure the maturity degree of a full mature compost. The method for measuring the maturity degree of a compost of this embodiment can fulfill biological, chemical and physical conditions in maturity to provide more overall and reliable assessment. In addition, based on the variation in absorbancy or the color contrasting density of a compost liquid phase, the maturity degree can be measured according to the maturity stage. By defining the absorbancy or color contrasting density as indices, higher-quality composts can be produced.

The measuring solution used in this embodiment is a solution can flocculate a compost extract containing humic-like substance and decomposed organic matter extracted from a composted material and reduce the absorbancy of a liquid phase as the compost becomes more mature. More specifically, salt concentration ranges from approx. from 0.2M to 2.0M, and pH value is under 8.0, and preferably it is 7 or less. When it is visually measured, the solution is preferably a buffer solution whose pH value is 4.0 or less.

Since this invention can stably and readily measure the maturity degree of all types of composts having different raw materials from garbage, food residue, livestock manure, etc, a liquid reagent specified herein is preferably a pH-adjustable solution such as an acetic acid-sodium acetate buffer solution with a pH value of under 0.8 containing a sodium chloride of at least 0.2M or more. More preferably, it is an acetic acid-sodium acetate buffer solution with a pH value of 4.0 containing a sodium chloride of 0.5M or more in view of the ability to visually measure the maturity degree. Most preferably, the reagent is a 0.2M acetic acid-sodium acetate buffer solution with a pH value of 4.0 containing a sodium chloride of 1.0M or more.

Meanwhile, the reagent is not limited to an acetic acid-sodium acetate buffer solution, and a solution containing a sodium chloride of 0.2M to 2.0M or even a phosphate buffer solution according to the type of a compost sample. Also, using a solution ranging from pH4.0 to 8.0, the maturity degree can be relatively measured according to compost sample. Even a solvent of high salt concentration (pH3.17 to 5.82) containing sodium sulfate, potassium chloride, manganous chloride, etc. or another solvent containing calcium carbonate and magnesium sulfate (pH3.17 to 5.82) showed a similar flocculation reaction, thereby achieving the determination of the maturity degree of a compost. However, a solvent used is preferably a low-cost sodium chloride.

Specifically in the method for measuring the maturity degree of a compost using the measuring solution in this invention, after a certain type of compost is added to the measuring solution, it is agitated for about 2 minutes and incubated for approx. 8 minutes. Then, after a humic-like substance, etc. extracted from the compost is flocculated, the color contrasting density of a liquid phase acquired by the solid-liquid separation using a centrifugal separator is checked with a prepared color sample to measure the maturity degree of a compost according to the maturity stage.

The agitating operation is not specifically limited if the compost and measuring solution are mixed to flocculate the humic-like substance, etc. This operation can be sufficiently achieved by adding the measuring solution to a plastic test tube of about 50 ml containing the compost and mixing the solution by shaking it with hands up and down.

The centrifugal separator is not limited if it has a solid-liquid separation ability to precipitate flocculated humic-like substance, etc. extracted from the compost, but in view of easy and swift operation in compost production and distribution by any user, small-sized portable centrifugal separator is preferably used. The centrifugal separator is not limited if the frequency and time of rotation in centrifugal separating operation are suited to solid-liquid separation, but it is designed to sufficiently separate the substance for about 10 minutes in 3,000 to 4,000 rotations and for about 1 to 2 minutes in 5,000 to 8,000 rotations.

The maturity degree of a compost by the color contrasting density of a liquid phase can be visually measured by checking it with a prepared color sample showing the relationship between a color of a liquid phase and the maturity degree of a compost. Also, the absorbancy can be measured by a spectrophotometer and obtained by comparing with pre-analyzed absorbancy data.

As shown in FIG. 2, 4-grade color samples, showing the relationship between a color of a liquid phase and the maturity degree of a compost, were prepared and classified into immature (early composting), middle mature, late mature and full mature. As the compost becomes more mature, the hue of a liquid phase changes blackish brown to more transparent amber. In order to measure the maturity degree without special expertise or skills, color samples can be made in quick reference chart, as shown in FIG. 3. In this quick reference chart, color series 1 and 2 are prepared. The color samples correspond to any color of composts from various raw materials, i.e. brown color series 1 mainly for cow's excreta and brown and greenish color series 2 for food residue. After any compost full maturity, it finally shows yellowish and transparent amber color with an absorbancy of 0.11 or less.

The measurement of the transmissivity and absorbancy using the spectrophotometer found stable values in the wavelength of 400 to 500 nm. In the wavelength of 400 nm or less, however, the transmissivity rapidly declines, with a transmissivity of 58.5% in 280 nm. Due to a transmissivity of 100% in 500 nm or more, the wavelength of the absorbancy to be measured is preferably 400 to 500 nm, and more preferably 465 nm.

Concerning the relationship between the absorbancy of a compost liquid phase and maturity degree, as shown in FIG. 2, when the compost was measured in the wavelength of 465 nm, it was immature (early composting) with an absorbancy of 0.35 or more. When the absorbancy ranged from 0.21 to 0.35, the compost was middle mature. When the absorbancy ranged from 0.11 to 0.21, the compost was late mature, and when the absorbancy was 0.11 or less, the compost was full mature, with hue visually identified.

The absorbancy showing said maturity degree was 0.11 or less in an experiment using mature composts according to conventional phytotoxicity test and method for measuring the maturity degree based on chemical properties. This observation validates the absorbancy in early composting ranging from 0.94 to 0.95, and that in middle composting ranging from 0.21 to 0.30.

Moreover, in this embodiment, by using composts collected throughout Japan as shown in FIG. 1, the absorbancy of a liquid phase of a full mature compost (maturity is proved according to chemical property test, etc.) was found 0.05 to 0.08, which is under 0.11 of full mature composts. As an index of phytotoxicity, the growth rate of root hair exceeded an appropriate range of 80% or more, and EC value showing a chemical property was under an appropriate value of 5.0 MS/CM. In immature composts with an absorbancy of 0.21 or more, biological, chemical and physical properties such as plant growth rate, EC value and moisture content didn't correspond to conventional maturity measuring indices.

As shown in FIG. 1, when the absorbancy of a liquid phase of a full mature compost was 0.11 or less, no phytotoxicity was confirmed and the average ammonium nitrogen content was 47.1 MG/100 G. This reduction is about 20% of the ammonium nitrogen content in an immature compost whose absorbancy is 0.11 or more. The nitrate nitrogen content was 14.0 MG/G, and it was reduced by about 40% compared to the immature compost.

Next, the method for measuring the maturity degree of a compost and the measuring solution of this embodiment with examples and experiments will be described.

Example 1

"Temperature Measurement, Chemical Property Analysis and Absorbancy Measurement in Composting Test"

As an example of this embodiment, the compost quality in a composting test was measured. First of all, a composting test and chemical property test were conducted in three test locations of A, B and C in which a subsidiary material was added to cow's excreta. The test location A is a group in which a composted material was aerated with chaff as a subsidiary material and turned at a composting temperature of 60 to 65° C., the test location B is a group in which a composted material was aerated and turned with wood waste as a subsidiary material at a composting temperature of 60 to 65° C. and the test location C is a group in which a composted material was merely heaped with mulch added thereto as a subsidiary material as a control group.

"Temperature Measurement in Composting Test"

Firstly, composting tests were performed in the test locations A, B, C using a 3.0 m3 box-type composting apparatus having a blower pump and exhaust port thereunder. The temperature within the facility was kept at 5° C. or more, the composting temperature was up to 65° C. to turn a composted material and the composting lasted for about 90 days.

As a result, as shown in FIG. 4, the composting temperature initially increased and then rapidly declined by turning. It repeatedly increased and decreased, resulting in gradual reduction in composting temperature. In the test locations A and B, the composting temperature became almost the same as the warehouse temperature 70 days after the test started, and mature process seemed to be completed. In order to completely kill pathogenic bacteria and weed seed in the batch composting process in these tests, the temperature must be kept at 55° C. for over three days. In these test locations A and B, a high temperature of 55° C. or more was maintained for over 10 days, demonstrating an observance of composting standards and a favorable composting. Meanwhile, in the test location C, a composting for achieving full maturity was not found due to insufficient temperature rise of up to 45° C. or so.

"Chemical Property Analysis in Composting Test"

Next, in each test location, a compost sample in the composting test was collected with time, and chemical properties were analyzed in compliance with the method for analyzing organic matter like composts. The compost sample was collected, soon, 7, 14, 21, 30, 61 and 91 days after the composting started.

Consequently, as shown in FIG. 5, the pH value increased in compost samples used in all the test locations during a period of 1 to 2 weeks after the composting started, and after pH temporarily declined, it showed a gradual increase. After EC value rapidly declined 2 to 3 weeks after the start of the composting, it demonstrated no significant changes. The moisture content showed a gradual decrease. In the test locations A and B, the moisture content was at a quality benchmark of 70% or less 90 days after the composting started. The organic matter content showed a gradual decrease, and it is suggested that a gradual decomposition of organic matter can promote composting. On the other hand, there were no changes in the above data in fertilizer components such as potassium, lime and magnesia.

Meanwhile, the observation of nitrogen transformation demonstrated an obvious difference in ammonium nitrogen and nitrate nitrogen as the composting proceeded. From early through late composting, the ammonium nitrogen content declined and instead the nitrate nitrogen was observed, thereby providing a favorable index of measuring the quality of a compost.

"Measurement of Absorbance in Composting Test"

Next, in each test location, the absorbancy was measured using compost samples of the composting test collected with time, based on the measuring solution of this embodiment. The measuring solution was a 0.2M acetic acid-sodium acetate buffer solution containing 1.0M sodium chloride with a pH value of 4.0. In the measurement, the measuring solution was added to a specific amount of a compost sample to achieve a mixture ratio of 1:2 (vol/vol) and the mixture was penetrated for approx. 10 to 15 minutes and was centrifugally separated at 3,000 rpm for 10 minutes. After diluting a supernatant (liquid phase) obtained 10 times in a distilled water, the absorbancy was measured at a wavelength of 465 nm.

As a result, as shown in FIGS. 5 and 6, in the full mature composts generated by aerating in the test locations A and B, the absorbancy swiftly declined before and after the completion of primary fermentation in which the composting temperature initially increased and then decreased. When the composting temperature rose and declined again upon completion of secondary fermentation, the absorbancy continued to decline. The absorbancy fell up to around 0.2, 60 days after the start of the composting. The growth rate of root hair, as an index of phytotoxicity, showed about 80% and the absorbancy was 0.11 or less on the $90^{th}$ day and the growth rate of root hair was 80% or more.

On the other hand, in merely heaped and no aerated composts of the test location C, the reduction in absorbancy even after secondary fermentation was small. The absorbancy was not at 0.35 or less even 90 days after the composting started. The growth rate of root hair was 58% on the $60^{th}$ day and 78.6% on the $90^{th}$ day, both of which didn't reach a proper range of 80%. From these observations, as shown in FIG. 5, it was found that there is a positive or negative correlation between the absorbancy and composting time required by day, proper composting process by the turning, temperature control, compost's biological, chemical or physical properties.

Example 2

"Relationship Between the Color and Concentration of Salt, Buffer Solution, pH or Absorbancy"

Next, compost's measuring solution will be discussed. The measuring solution was added to a compost sample in any of the following experiments to achieve a mixture ratio of 1:2 (vol/vol), and it was agitated for about 10 to 15 minutes. Afterward, the mixture was centrifugally separated at 3,000 rpm for 10 minutes, and a supernatant (liquid phase) obtained was diluted 10 times in a distilled water. The absorbancy was measured at a wavelength of 465 nm.

"Experiment 1: Examination 1 of Salt Concentration"

A basic experiment was conducted to examine the impact of salt concentration as a compost measuring solution. In three compost samples, in which the state of compost maturity was confirmed from the phytotoxicity test and chemical properties beforehand, a measuring solution with different salt concentrations was added thereto to discuss the effect. 3 compost samples are full mature product composts A and B, and middle mature compost C. The measuring solution was obtained by distilling a saturated solution having a 6.10M sodium chloride concentration twice to produce 4-level sodium chloride solutions of 3.070M, 1.535M, 0.767M, and a distilled water was used as a control group.

Consequently, as shown in FIG. 7, in the mature product composts A and B, the addition of a higher salt-concentration measuring solution changed the color of an extracted compost liquid phase from turbid blackish brown to transparent amber. On the other hand, the immature compost C demonstrated a dark brown color even with a measuring solution of high salt concentration and the color contrasting density of a compost liquid phase was not observed due to the change in salt concentration.

"Experiment 2: Examination 2 of Salt Concentration"

Figure 8:
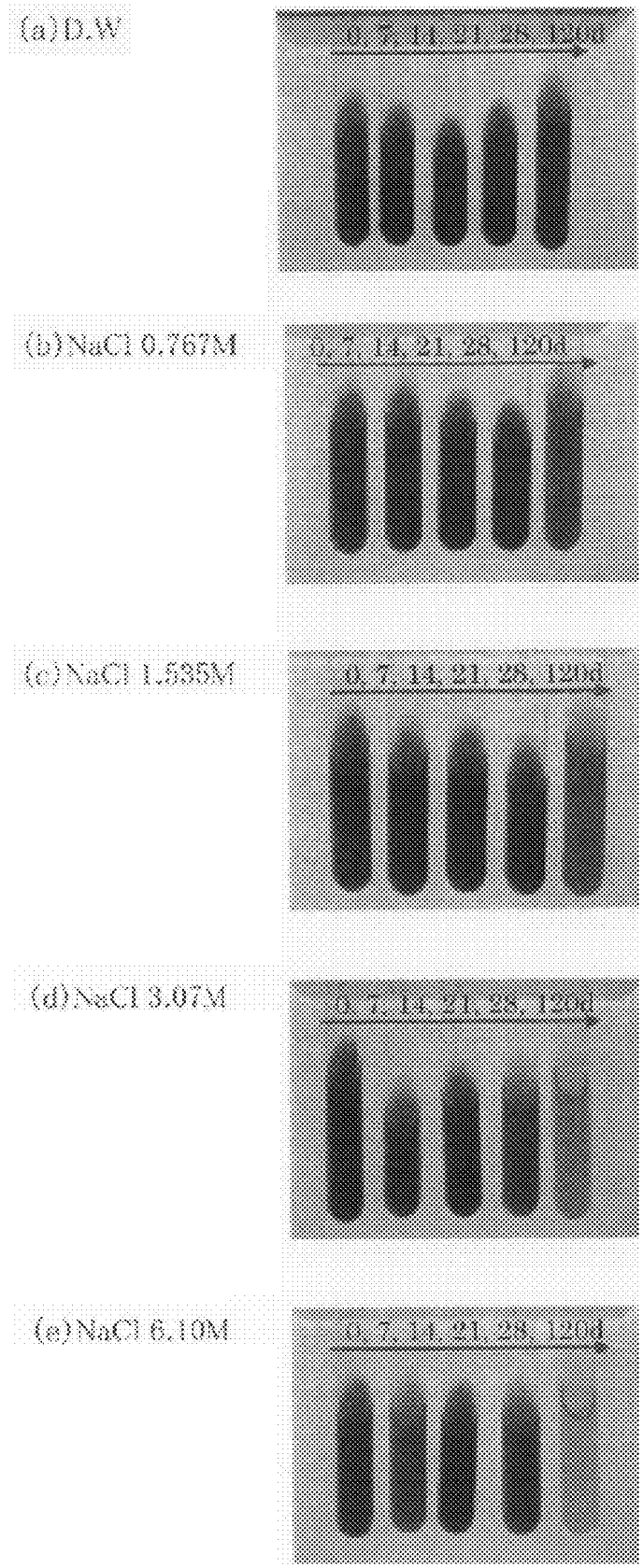
FIG. 8 is a digital photographic image showing the color contrasting density in the composting process in experiment 2 for obtaining the optimum salt concentration for a measuring solution in Example 2, and (a) is a digital photographic image for a distilled water, (b) is a digital photographic image for a salt concentration of 0.76M, (c) is a digital photographic image for a salt concentration of 1.535M, (d) is a digital photographic image for a salt concentration of 3.07M and (e) is a digital photographic image for a salt concentration of 6.10M.

Subsequently, from early through late composting, experiment 2 was conducted to examine the impact of salt concentration in the measuring solution. The measuring solution was different in salt concentration from that used in the above mentioned experiment 1. The compost samples were composted for 7, 14, 21, 28 and 120 days at the composting center. The results of the color contrasting density in the experiment 2 are shown in FIG. 8. The compost 120 days after composting is a mature compost according to conventional phytotoxicity tests and chemical properties.

As shown in FIG. 8, a measuring solution with a salt concentration of 0.767M to 6.10M showed various hue concentrations, but as a compost sample is overall composted, the hue of a compost liquid phase changed from blackish brown to transparent amber, resulting in the ability to visually measure the composting process.

In the meantime, regardless of the extent of composting in a distilled water, there was no change in turbid blackish brown color in the compost liquid phase. It was not possible to visually measure the difference among early, middle and late composting.

"Experiment 3: Relationship Between Absorbancy and Color of Compost Extraction Liquid Phase"

In the experiments 1 and 2 with the above salt concentrations, the relationship between the absorbancy and the color of a liquid phase was examined by measuring the absorbancy of each compost liquid phase at a wavelength of 465 nm.

As a result, as shown in FIG. 2, when the absorbancy was 0.35 or more, the color of the compost liquid phase was blackish brown. When the absorbancy was 0.11 to 0.35, the color was brown and the absorbance of under 0.11 showed transparent amber.

From these results, by raising the sodium chloride of the measuring solution, the reduction in absorbancy of the compost liquid phase by progressive composting was observed, and early composting and middle composting showed blackish brown and blackish brown or brownish, respectively, and full mature compost demonstrated transparent amber, resulting in the ability to visually confirm the change in color of a compost liquid phase.

"Experiment 4: Optimum Salt Concentration of Acetic Acid-Sodium Acetate Buffer Solution"

It was found that when the maturity degree is assessed by the absorbancy in the above experiments, the impact of salt concentration is significant. Then, this experiment 4 was performed to obtain more efficient measuring solution and the range of favorable salt concentration.

Firstly, 0.0, 0.2, 0.5, 0.7, 1.0, 2.0M sodium chloride solutions were added to a acetic acid-sodium acetate buffer solution to have different salt concentrations therein and produce measuring solutions. Then, these measuring solutions were added to a solvent containing a standard humic-like substance and two middle mature composts (composts C and D). Afterward, a compost extract was flocculated and then the absorbancy of a solid-liquid separated supernatant (liquid phase) was measured. The results are shown in FIGS. 9 and 10.

Figure 9:
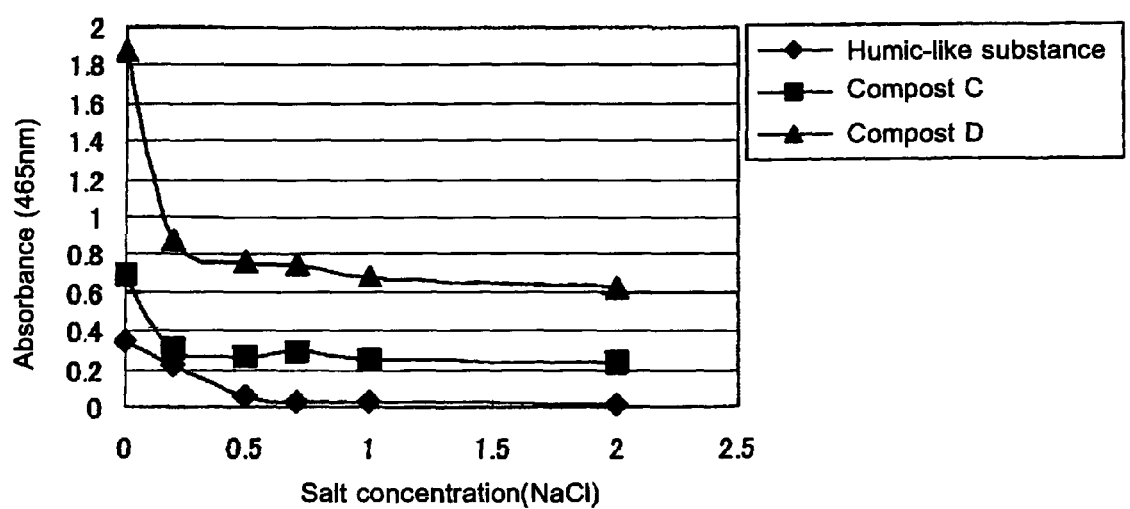
FIG. 9 is a graph showing the relationship between the change in salt concentration and the absorbancy in experiment 4 for obtaining the optimum salt concentration for a measuring solution in Example 2.
Figure 10:
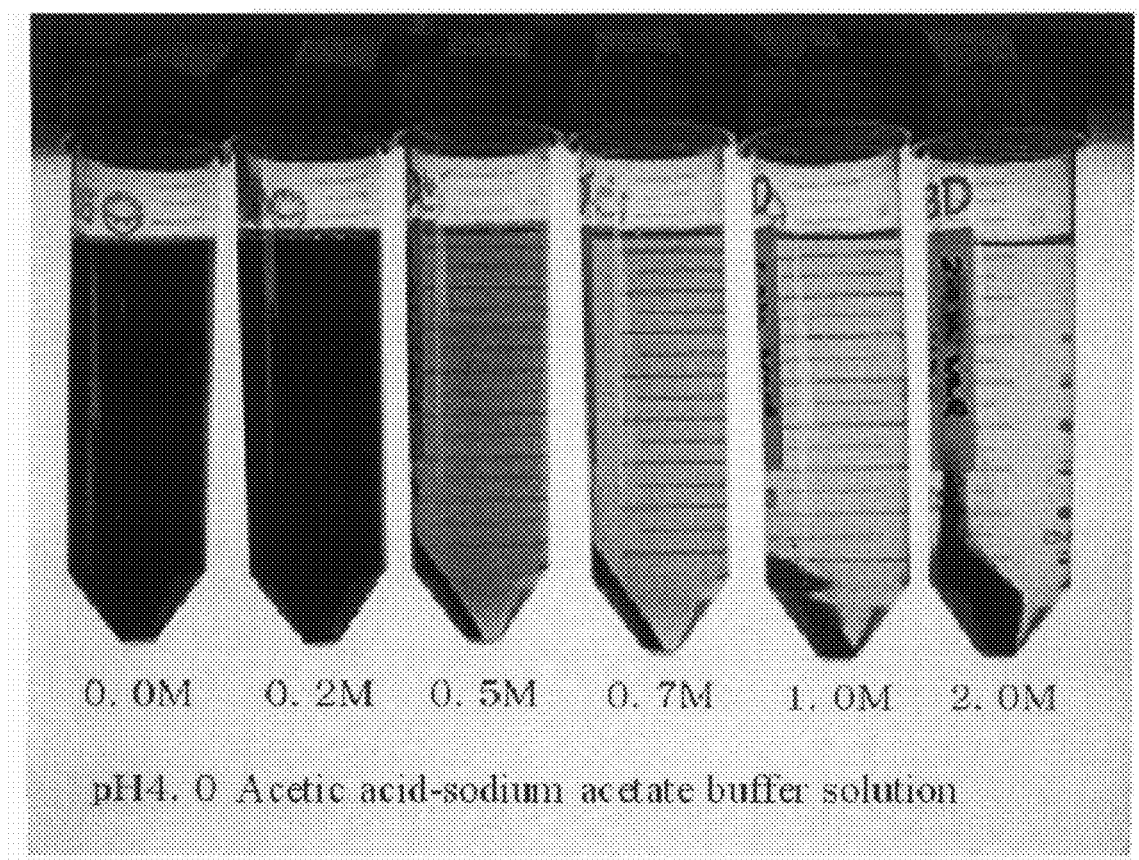
FIG. 10 is a digital photographic image showing the color contrasting density when salt concentration is changed in experiment 4 for obtaining the optimum salt concentration for the measuring solution in Example 2.

As shown in FIGS. 9 and 10, by adding a 0.2M-or-more sodium chloride to an acetic acid-sodium acetate, the flocculation of a humic-like substance obtained from a standard humic-like substance or compost was observed and the absorbancy was reduced. More specifically, as for a solvent containing the humic-like substance, an acetic acid-sodium acetate buffer solution having no sodium chloride or 0.0M salt concentration showed an absorbancy of 0.349. However, as a sodium chloride concentration increased, the absorbancy declined to 0.05 in 0.5M salt concentration, 0.034 in 0.7M salt concentration, 0.023 in 1.0M salt concentration and 0.015 in 2.0M salt concentration.

In the compost C, the absorbancy was 0.697 in 0.0M salt concentration, and reduced to 0.250 in 1.0M salt concentration. In the compost D, the absorbancy was 1.875 in 0.0M salt concentration, but it declined to 0.686 in 1.0M salt concentration.

In view of these results in a comprehensive manner, the sodium chloride concentration that can stably measure the change in color of compost liquid phase ranges from 0.7M to 2.0M, and the salt concentration showing more stable change in absorbancy is 1.0M or more.

"Experiment 5: Favorable pH Value"

Figure 12:
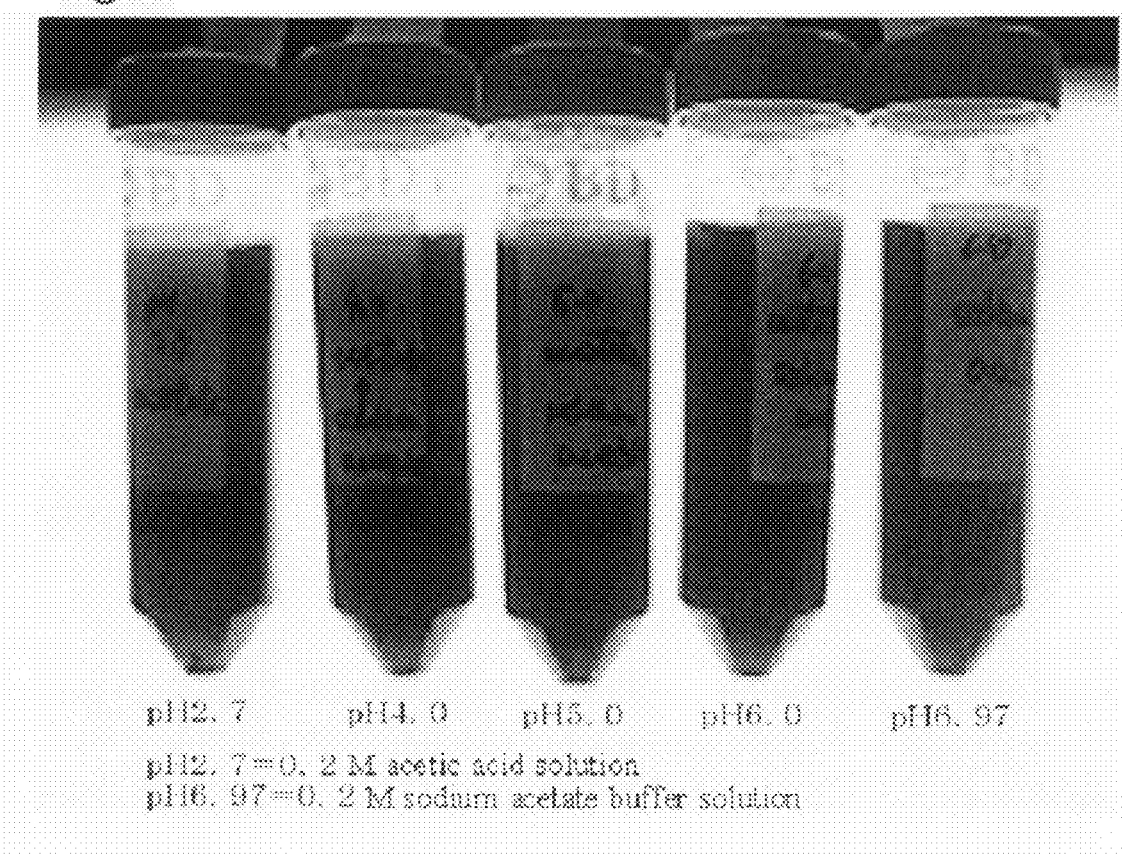
FIG. 12 is a digital photographic image showing the results of mature substances in experiment 5 for obtaining the optimum pH for the measuring solution in Example 2.
Figure 13:
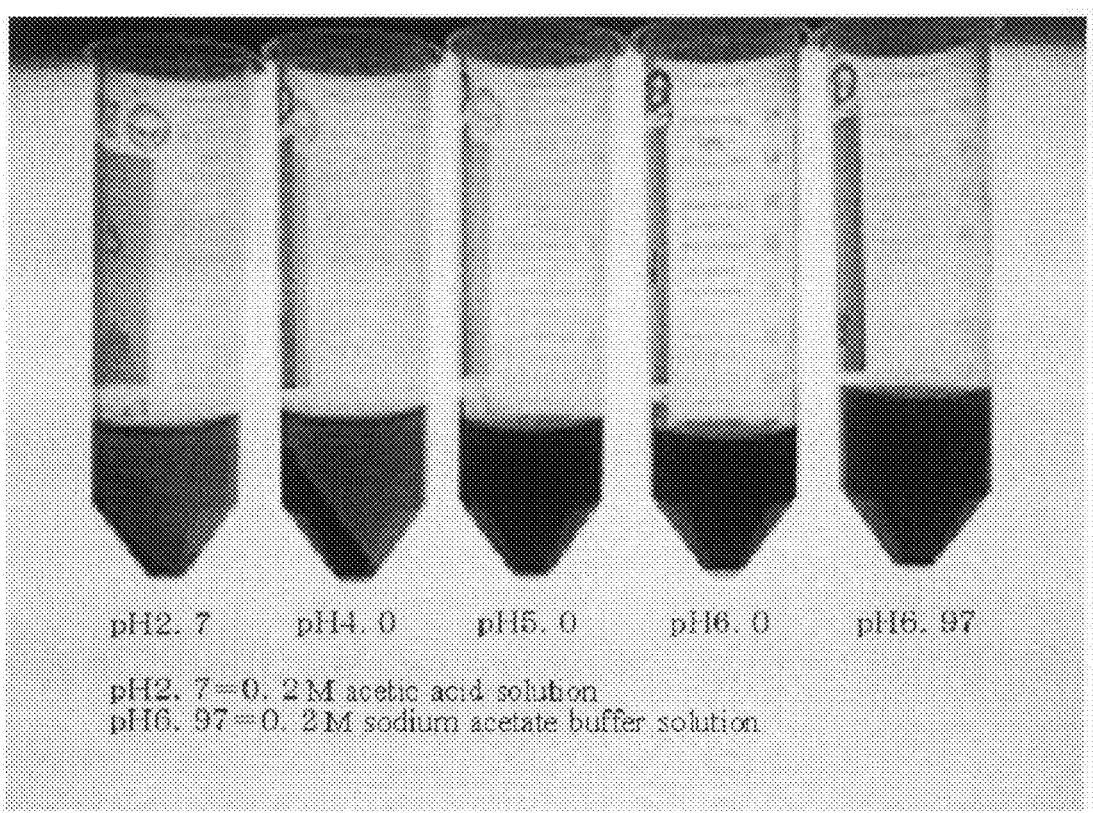
FIG. 13 is a digital photographic image showing the results of middle mature compost C in experiment 5 for obtaining the optimum pH for the measuring solution in Example 2.

Subsequently, an experiment was performed to obtain a favorable pH value for a measuring solution of acetic acid-sodium acetate. With a standard 0.2M acetic acid solution with a pH value of 2.7, a sodium acetate was added to the measuring solution used in the experiment to adjust pH, and resulting 0.2M acetic acid-sodium acetate buffer solutions having pH4.0, 5.0, 6.0 and 6.97 were each used. Also, as in the experiment 4, a solvent containing a standard humic-like substance and 2 middle mature composts (composts C and D) will be measured and the absorbancy was measured for the solid-liquid separation supernatant (liquid phase) in compost extracts. The results are shown in FIGS. 11 to 13.

Figure 11:
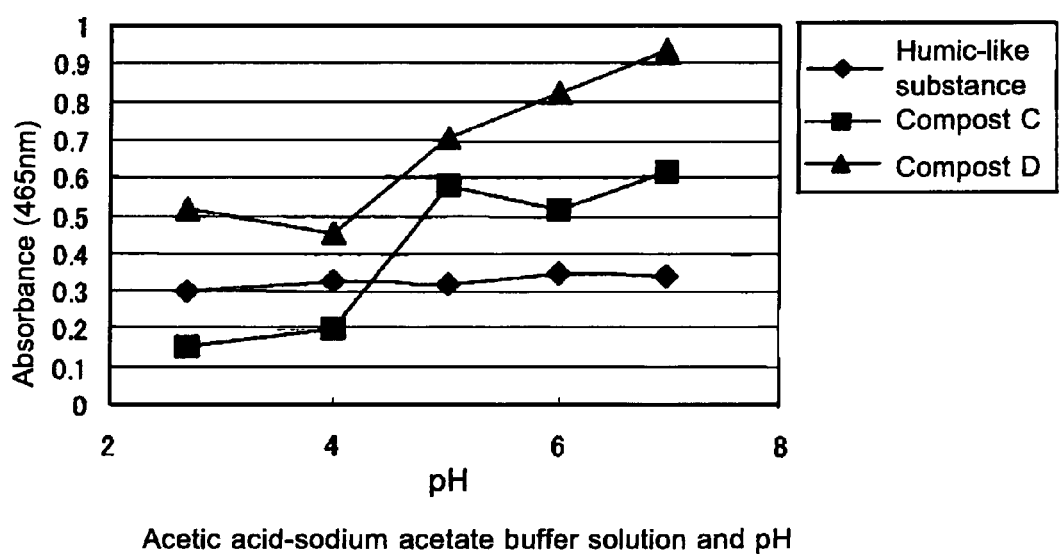
FIG. 11 is a graph showing the relationship between the change in pH and the absorbancy in experiment 5 for obtaining the optimum pH for a measuring solution in Example 2.

As shown in FIG. 11, an overall difference between the middle mature compost and mature compost is shown as a difference in absorbancy. Such a difference can be obviously demonstrated with a pH of 4.0 or less. For example, in an extract derived from middle mature compost, the absorbancy of a solid-liquid separated supernatant (liquid phase) in compost C was 0.618 in pH6.97, but declined to 0.203 in pH4.0. In the compost D, the absorbancy was 0.938 in pH6.97, and declined to 0.456 in pH4.0. In the meantime, a solvent containing a standard humic-like substance showed only the slope of pH, but no flocculation reaction, and the change in absorbancy was small from 0.302 to 0.349. The flocculation of humic-like substance requires the addition of a salt-containing measuring solution. As shown above, using the range of pH value tested, an overall difference between the full mature compost and middle mature compost is found to enable the measurement of the maturity degree. Particularly, the absorbancy becomes stable in a pH of 4.0 or less, resulting in the ability to readily visually measure the maturity degree.

The absorbancy of a full mature liquid dphase in pH8.0 ranges from 0.180 to 0.233, and it is difficult to measure the compost maturity from the color contrasting density. However, since the absorbancy declines in early, middle composting and full mature compost by adding salt to a solution, the maturity degree can be measured by the spectrophotometer.

As shown in FIGS. 9 to 13, the measuring solution includes 1.0M-or-so salt concentration. The use of this measuring solution is preferable, because if the solution has a pH of 4.0 or less, the maturity degree can be visually measured from the flocculation reaction of a humic-like substance or compost extract.

As for mature composts E, F, G and middle mature compost H determined in previously-known phytotoxicity test and chemical properties, a 1.0M sodium chloride was added to an acetic acid-sodium acetate solution to set pH at 4.0, and the absorbancy was measured from a compost liquid phase. As a result, as shown in FIG. 14, in composts E, F and G with a growth rate of root hair of 80% or more, the absorbancy ranged from 0.033 to 0.069, that is under 0.11 as an index of the absorbancy in the full mature compost. In the middle mature compost H, the absorbancy was 0.328, with no growth of root hair and no germination rate of a benchmark 80%.

When the correlation between the absorbancy and plant germination rate in the compost sample was examined, as shown in FIG. 15 (A) to (C), the correlation in the pH4.0 measuring solution was high, compared in pH5.0 or pH8.0.

From these observations, if the pH of a measuring solution ranges from at least pH2.7 to pH4.0, the flocculation of a compost extract can reduce the absorbancy, and the preparation of 1.0M-or-so salt concentration can assuredly observe absorbancy reduction and color contrasting density.

Example 3

"Measurement of the Maturity Degree in Non-Excreta Raw Materials"

By examining salt concentration and pH of the above mentioned measuring solutions, the use of a measuring solution with a salt concentration of 1.0M and pH4.0 shows a visually identifiable and obvious difference in hue of liquid phase obtained from excreta-derived composts and compost sample in the composting process according to the maturity stage. Then, to examine the possibility of measuring the maturity degree in composts derived from non-excreta raw materials, the absorbancy and color contrasting density of compost samples in the composting process in the test locations A, B and C were observed.

The compost samples are chaff-derived in the test location A, wood waste-derived in the test location B and a mixture of cow excreta and mulch in the test location C. In the test locations A and B, the temperature was initially set at 55° C. and raised for 3 or more days and additional aeration produced favorably full mature compost. In the test location C, the composts were only heaped, and the fermentation temperature was not raised up to 55° C. or more, thereby achieving insufficiently composted immature composts. Early, middle and late composting were each set according to the absorbancy, germination rate and growth rate of root hair.

Consequently, as shown in FIG. 16, in favorably composting test locations A and B, the absorbancy declined with time, and it was 0.15 or less 90 days after the start of composting. The color of a compost liquid phase changed from blackish brown to transparent amber. On the other hand, in the test location C with no favorable composting, the reduction in absorbancy was not found even 90 days after the start of composting, and the color of the compost liquid phase was brownish, not transparent amber.

Also, as shown in FIG. 17, in the composing with raw materials of wood waste and food residue, the growth rate of root hair was 0.0%, the germination rate was 13.3%, the absorbancy was 0.497 on the $30^{th}$ day after the start of composting. However, 180 days after the start of composting, the growth rate of root hair was 90.0%, the germination rate was 93.3% and the absorbancy was 0.095. The chemical and physical properties didn't depart from standard values, and the composts were found full mature.

From the above results, the measuring solution with 1.0M sodium chloride concentration and pH4.0 determined the absorbancy of a compost liquid phase and change in color not only for excreta, but also for chaff- or wood waste-derived composts, and composting containing food residue. Since these data have correlations with the maturity degree according to phytotoxicity tests and chemical properties, the possibility of measuring the maturity degree in view of plant growth, chemical and physical properties was confirmed.

Example 4

"Phytotoxicity and Absorbancy"

Next, to examine the relationship between the germination rate, root growth (main root and root hair growth) rate, and the absorbancy of a compost liquid phase in the phytotoxicity test, composts mixed with cow's excreta and rice straw, dried composts mixed with cow's excreta and wheat, composts mixed with crab husk and wood waste and food residue composts were used.

As for the growth rate of root hair, component extraction was conducted from a 10 G compost using a 100 ml hot liquid, and komatusna is seeded in compost extraction medium containing 1.0% agar, and the compost was incubated at 23° C. in the gross cabinet for 5 days to measure the growth rate of root hair by comparing with a control zone. At the same time, the absorbancy was measured in the compost sample using the measuring solution.

As a result, as shown in FIG. 18, as germination and root growth rates increased, the absorbancy linearly declined. The compost having higher germination and root growth rates showed no phytotoxicity, and it was found to be a full mature fertilizer with a high maturity degree. Therefore, as plant main root and root hair growth rates increased, the absorbancy of a compost liquid phase declined. Based on this correlation, the maturity degree of a compost can be measured.

Example 5

"Change in Nitrogen Form and Absorbancy"

Next, the relationship between the nitrogen transformation and absorbancy was examined. As organic matter such as compost is decayed or matured, the possibility of using nitrogen transformation as a method for measuring the maturity degree of organic materials is suggested. Even in a chemical property test of composting, nitrogen transformation was observed as composing proceeded. Then, nitrogen transformation was examined when the absorbancy was reduced as composting proceeded.

The nitrogen was extracted by a commonly-known acid hydrolysis, and was measured by a nitrogen gauge. The ammonium nitrogen and nitrate nitrogen were similarly measured.

As a result, as shown in FIGS. 1 and 5, the ammonium nitrogen declined as the absorbancy decreased (composting time required by day) and nitrate nitrogen came to existence. Thus, when the absorbancy was 0.11 or less, the compost can be found to be a full mature compost with reduction in both ammonium nitrogen and nitrate nitrogen.

Example 6

"Compost and Absorbancy According to Difference in Regional Characteristics and Raw Materials"

As for a plurality of compost samples having different regional characteristics and raw materials, the maturity degree is classified into early composting (immature), middle mature and late mature (full mature) by interviewing from each composting center administrator to analyze the absorbancy, phytotoxicity test and chemical properties.

As a result, as shown in FIG. 19, in a compost group with an absorbancy of 0.11 or less, no phytotoxicity was found, and chemical properties also showed the results equivalent to proper values. The nitrogen transformation, indicating the reduction in ammonium nitrogen and nitrate nitrogen, was observed. Then, growth rates of main root and root hair showed 88.87% and 95.78%, respectively, within an appropriate value of 80.0% or more. Meanwhile, in a middle mature compost with an absorbancy of 0.11 to 0.35, the growth rates of main root and root hair were 62.43% and 61.83%, respectively. In a immature compost group having an absorbancy of 0.35 or more, the growth rates of main root and root hair were 22.90% and 17.86%, respectively, showing an obvious growth inhibition.

As shown in each of the above examples, composting time required by day, temperature control and management of processes such as turning, compost properties (biological, chemical and physical) and the reduction in absorbancy were found to have correlations in this invention.

In this embodiment according to the above descriptions, the following technical advantages can be obtained.

1. The measurement merely requires mixing a measuring solution with a compost and centrifugally separating to compare with a color sample. No special analytical or measuring apparatus is required.

2. The maturity degree of a compost can be measured according to each maturity stage.

3. The maturity degree can be measured without special expertise or experience for analysis or measurement.

4. The maturity degree of a compost can be measured on the spot in a short period of time of 10 to 30 minutes.

Despite a longer composting time required by day, when the absorbancy is high according to a method for measuring the maturity degree of a compost of this embodiment or the compost doesn't show maturity completion, it is swiftly possible to find out the factors in immaturity, such as appearance of immature compost due to failed moisture content adjustment and insufficient ventilation by insufficient turning or aeration.

With this advantage, agriculture associated organizations, etc. can instruct agricultural crop producers and those engaged in livestock in farming management, greatly contributing to the production of reliable and safe agricultural and livestock products. In the meantime, compost users can use no poor-quality (immature) composts associated with plant growth inhibition and increase a cropping area by using high-quality (full mature) composts, leading to wider compost distribution. Moreover, the risk of nitrogen contamination due to nitrate nitrogen, etc. caused by the use of poor-quality composts and chemical fertilizers combined can be reduced by properly performing compost quality management. This method can also prevent nitrate pollution in the quality of underground water, rivers and lakes, establish sustainable farming system (prepare favorable farm land) with reduced environmental contamination on soil and ensure food safety.

The method for measuring the maturity degree of a compost and measuring solution of this invention are not intended as a definition of the limits of the above described embodiment, but may be modified accordingly.

What is claimed is:

1. A method for measuring the maturity degree of a compost, comprising the steps of
    adding a predetermined measuring solution to a compost to flocculate a compost extract containing a humic-like substance and decomposed organic matter;
    obtaining a liquid phase by precipitating said compost extract by a solid/liquid separation; and
    measuring the maturity degree of said compost from the color contrasting density of said liquid phase, based on the correlation in which the absorbancy of said liquid phase declines as said compost becomes more mature.

2. The method for measuring the maturity degree of a compost set forth in claim 1, wherein:
    the maturity degree of said compost is measured from the color contrasting density of said liquid phase, based on the correlation in which the absorbancy of said liquid phase declines according to nitrogen transformation that causes nitrate nitrogen as ammonium nitrogen of said compost decreases, and according to a method for measuring the maturity degree with reference to biological, chemical and physical properties of said compost.

3. The method for measuring the maturity degree of a compost set forth in claim 1, wherein:

the maturity degree of said compost is measured from the color contrasting density of said liquid phase, based on the correlation in which the absorbancy of said liquid phase declines as the growth rates of a plant main root and root hair grown using said compost increase.

4. The method for measuring the maturity degree of a compost set forth in any one of claims 1 to 3, wherein:

said measuring solution is a solution whose salt concentration ranges from 0.2M to 2.0M.

5. The method for measuring the maturity degree of a compost set forth in claim 4, wherein:

said measuring solution is a solution whose pH value is 7.0 or less.

6. The method for measuring the maturity degree of a compost set forth in claim 5, wherein:

said measuring solution is an acetic acid-sodium acetate buffer solution.

7. The method for measuring the maturity degree of a compost set forth in claim 1, wherein:

the maturity degree of said compost is measured by using a colorimetric sample by which the color contrasting density of said liquid phase and the maturity degree of said compost are associated with each other beforehand.

8. A measuring solution for measuring the maturity degree of a compost, comprising:

means for obtaining a liquid phase by mixing said measuring solution with said compost to flocculate a humic-like substance and decomposed organic matter to visually determine the degree of maturity from an absorbency of the liquid phase, wherein;

said measuring solution is an acetic acid-sodium acetate buffer solution with a sodium chloride concentration ranging from 0.2M to 2.0M and a pH value of 7.0 or less.

9. A measuring solution for measuring the maturity degree of a compost, comprising:

means for obtaining a liquid phase by mixing said measuring solution with said compost to flocculate a humic-like substance and decomposed organic matter to visually measure the maturity degree from an absorbancy of said liquid phase, wherein;

said measuring solution is a 0.2M acetic acid-sodium acetate buffer solution with a sodium chloride concentration of 1.0M and a pH value of 4.0.

* * * * *